(12) United States Patent
McGrath

(10) Patent No.: US 7,811,234 B2
(45) Date of Patent: Oct. 12, 2010

(54) REMOTE-SENSING METHOD AND DEVICE

(75) Inventor: William R. McGrath, Monrovia, CA (US)

(73) Assignee: California Institute of Technology, Pasadena, CA (US)

(*) Notice: Subject to any disclaimer, the term of this patent is extended or adjusted under 35 U.S.C. 154(b) by 147 days.

(21) Appl. No.: 11/897,884

(22) Filed: Aug. 30, 2007

(65) Prior Publication Data

US 2008/0045832 A1 Feb. 21, 2008

Related U.S. Application Data

(63) Continuation-in-part of application No. 10/632,347, filed on Aug. 1, 2003, now Pat. No. 7,272,431.

(60) Provisional application No. 60/400,399, filed on Aug. 1, 2002, provisional application No. 60/473,670, filed on May 23, 2003, provisional application No. 60/841,765, filed on Aug. 31, 2006.

(51) Int. Cl.
*A61B 5/02* (2006.01)
(52) U.S. Cl. .................................................. 600/508
(58) Field of Classification Search .................. 600/407, 600/425, 426, 427, 429, 430, 428, 595, 534, 600/547, 508; 324/638, 642, 644; 702/20, 702/57; 435/6, 7.1; 606/33
See application file for complete search history.

(56) References Cited

U.S. PATENT DOCUMENTS 4,488,559 A * 12/1984 Iskander ..................... 600/430
4,833,918 A * 5/1989 Jean et al. .................. 73/290 V (Continued)

FOREIGN PATENT DOCUMENTS

EP 1 188 412 A2 3/2002

(Continued)

OTHER PUBLICATIONS

Clark et al., "Medical Instrumentation Application And Design", John Wiley & Sons, Inc., undated, Third Edition, Section 4.6 through 6.6, pp. 139-259, Cover p. 1.

(Continued)

*Primary Examiner*—George Manuel
*Assistant Examiner*—Robert N Wieland
(74) *Attorney, Agent, or Firm*—Christie, Parker & Hale, LLP

(57) ABSTRACT

A remote-detection system is provided for monitoring changes in permittivity associated with physiological activity of a subject that is free to move. The system includes a source containing an oscillator configured to illuminate tissue of the subject with an electromagnetic signal beam. The system further includes a receiver configured to receive reflections of the electromagnetic signal beam from the subject. The reflections include amplitude variations indicative of motion of the illuminated tissue and amplitude variations indicative of time dependent variations in the permittivity of the illuminated tissue associated with electrical activity of the subject's heart. The system further includes a detector connected to the receiver and configured to extract from the reflected signal beam the variations in amplitude indicative of motion of the illuminated tissue or indicative of time dependent variations in the permittivity of the illuminated tissue associated with the electrical activity of the subject's heart.

19 Claims, 24 Drawing Sheets

U.S. PATENT DOCUMENTS

| | | | |
|---|---|---|---|
| 4,958,638 A | 9/1990 | Sharpe et al. | |
| 5,030,956 A | 7/1991 | Murphy | |
| 5,105,354 A | 4/1992 | Nishimura | |
| 5,226,425 A | 7/1993 | Righter | |
| 5,227,797 A | 7/1993 | Murphy | |
| 5,363,050 A * | 11/1994 | Guo et al. | 324/638 |
| 5,448,501 A | 9/1995 | Hablov et al. | |
| 5,507,291 A | 4/1996 | Stirbl et al. | |
| 5,606,971 A | 3/1997 | Sarvazyan | |
| 5,760,687 A | 6/1998 | Cousy | |
| 5,931,791 A | 8/1999 | Saltzstein et al. | |
| 6,011,477 A | 1/2000 | Teodorescu et al. | |
| 6,031,482 A | 2/2000 | Lemaitre et al. | |
| 6,062,216 A | 5/2000 | Corn | |
| 6,083,172 A | 7/2000 | Baker, Jr. et al. | |
| 6,122,537 A | 9/2000 | Schmidt | |
| 6,129,675 A | 10/2000 | Jay | |
| 6,132,371 A | 10/2000 | Dempsey et al. | |
| 6,208,286 B1 | 3/2001 | Rostislavovich et al. | |
| 6,254,551 B1 | 7/2001 | Varis | |
| 6,289,238 B1 | 9/2001 | Besson et al. | |
| 6,315,719 B1 | 11/2001 | Rode et al. | |
| 6,325,761 B1 | 12/2001 | Jay | |
| 6,332,087 B1 * | 12/2001 | Svenson et al. | 600/407 |
| 6,359,597 B2 | 3/2002 | Haj-Yousef | |
| 6,377,201 B1 * | 4/2002 | Chu | 342/22 |
| 6,434,411 B1 | 8/2002 | Duret | |
| 6,454,708 B1 | 9/2002 | Ferguson et al. | |
| 6,478,744 B2 | 11/2002 | Mohler | |
| 6,753,780 B2 | 6/2004 | Li | |
| 2002/0028991 A1 | 3/2002 | Thompson | |
| 2004/0019261 A1 | 1/2004 | Gopinathan et al. | |
| 2005/0073424 A1 * | 4/2005 | Ruoss et al. | 340/686.6 |
| 2008/0045832 A1 * | 2/2008 | McGrath | 600/427 |

FOREIGN PATENT DOCUMENTS

| | | |
|---|---|---|
| WO | WO 93/19667 | 10/1993 |
| WO | WO 02/05700 A2 | 1/2002 |

OTHER PUBLICATIONS

Geddes et al., "Principles Of Applied Biomedical Instrumentation", Wiley-Interscience Publication, Third Edition, undated, pp. 600-613, cover p. 1.

IEEE Standards Coordinating Committee 28, "IEEE Standard For Safety Levels With Respect To Human Exposure To Radio Frequency Electromagnetic Fields, 3kHz to 300 GHz", IEEE Std. C95.1, Apr. 16, 1999, pp. 1-73, Cover p. 1, Abstract (2 pgs), Introduction (6 pgs), Table of Contents (1 pg).

Behnia et al., "Closed-Loop Feedback Control of Phased-Array Microwave Heating Using Thermal Measurements From Magnetic Resonance Imaging", Concepts in Magnetic Resonance (Magnetic Resonance Engineering ), vol. 15, No. 1, 2002, pp. 101-110.

Osepchuk, J., "How Safe Are Microwaves And Solar Power From Space?", IEEE Microwave Magazine, Dec. 2002, pp. 58-64.

Yan et al., "Theoretical Analysis Of The Biological Thermal Effect Of Millimeter Waves In Layered-Dielectric-Slabs", International Journal of Infrared and Millimeter Waves, vol. 24, No. 5, May 2003, pp. 763-772.

Vijayalaxmi et al., "Genotoxic Potential Of 1.6 GHz Wireless Communication Signal: In Vivo Two-Year Bioassay", Radiation Research, vol. 159, 2003, pp. 558-564.

Bit-Babik et al., "Estimation Of The SAR In The Human Head And Body Due To Radiofrequency Radiation Exposure From Handheld Mobile Phones With Hands-Free Accessories", Radiation Research, vol. 159, 2003, pp. 550-557.

Thalau et al., "Temperature Changes In Chicken Embryos Exposed To A Continuous-Wave 1.25 GHz Radiofrequency Electromagnetic Field", Radiation Research, vol. 159, 2003, pp. 685-692.

Hirata et al., "Correlation Of Maximum Temperature Increase and Peak SAR In The Human Head Due to Handset Antennas", IEEE Transactions On Microwave Theory and Techniques, vol. 51, No. 7, Jul. 2003, pp. 1834-1841.

Lin et al., "Wearable Sensor Patches For Physiological Monitoring", JPL Inventor's Report, NASA Case No. 0246 2065I, NASA Tech Brief vol. 25, No. 2, pp. 1-3, cover pgs (2).

Patterson, R. "Fundamentals Of Impedance Cardiography", IEEE Engineering In Medicine and Biology Magazine, Mar. 1989, pp. 35-38.

Wang et al., "Multiple Sources Of The Impedance Cardiogram Based On 3-D Finite Difference Human Thorax Models", IEEE Transactions on Biomedical Engineering, vol. 42, No. 2, Feb. 1995, pp. 141-148.

Patterson et al., "Impedance Cardiography Using Band And Regional Electrodes In Supine, Sitting, And During Exercise", IEEE Transactions on Biomedical Engineering, vol. 38, No. 5, May 1991, pp. 393-400.

Jossinet, J., "The Impedivity Of Freshly Excised Human Breast Tissue", Physiol. Meas., vol. 19, 1998, pp. 61-75.

Mohapatra et al., "Blood Resistivity And Its Implications For The Calculation Of Cardiac Output By The Thoracic Electrical Impedance Technique", Intens. Care Med., vol. 3, 1977, pp. 63-67.

King R., "Comments On Biological Effects Of Radio-Frequency/Microwave Radiation", IEEE Transactions on Microwave Theory and Techniques, vol. 50, No. 8, Aug. 2002, pp. 2032-2033.

King, R., "Electric Fields Induced In Cells In The Bodies Of Amateur Radio Operators By Their Transmitting Antennas", IEEE Transactions On Microwave Theory and Techniques, vol. 48, No. 11, Nov. 2000, pp. 2155-2158.

King, R., "Electric Current And Electric Field Induced In The Human Body When Exposed To An Incident Electric Field Near The Resonant Frequency", IEEE Transactions on Microwave Theory and Techniques, vol. 48, No. 9, Sep. 2000, pp. 1537-1543.

Johnson et al., "Nonionizing Electromagnetic Wave Effects In Biological Materials And Systems", Proceedings of the IEEE, vol. 60, No. 6, Jun. 1972, pp. 692-719.

Lohman et al., "A Digital Signal Processor For Doppler Radar Sensing Of Vital Signs", 2001 Proceedings of the 23rd Annual EMBS International Conference, Oct. 25-28, 2001, Istanbul, Turkey, pp. 3359-3362.

Guillen et al., "Design Of A Prototype For Dynamic Electrocardiography Monitoring Using GSM Technology: GSM-Holter", 2001 Proceedings of the 23rd Annual EMBS International Conference, Oct. 25-28, 2001, Istanbul, Turkey, pp. 3956-3959.

Marbán, E., "Cardiac Channelopathies", Insight Review Articles, undated, 6 pgs.

Boric-Lubecke et al, "Wireless House Calls: Using Communications Technology For Health Care And Monitoring", IEEE Microwave Magazine, Sep. 2002, pp. 43-48.

Holden, A., "A Last Wave From The Dying Heart", Nature, vol. 392, Mar. 5, 1998, pp. 20-21.

Abubakar et al., "Imaging of Biomedical Data Using A Multiplicative Regularized Contrast Source Inversion Method", IEEE Transactions on Microwave Theory and Techniques, vol. 50, No. 7, Jul. 2002, pp. 1761-1771.

Yu et al., "Can Millimeter Waves Generate Electroporation?", International Journal of Infrared and Millimeter Waves, vol. 23, No. 8, Aug. 2002, pp. 1261-1269.

Yu et al., "Discussion About The Ratio Method For Measuring Millimeter Wave Absorption By Biological Entities", International Journal of Infrared and Millimeter Waves, vol. 23, No. 7, Jul. 2002, pp. 997-1006.

McGill et al., "A Model Of The Muscle Action Potential For Describing The Leading Edge, Terminal Wave, And Slow Afterwave", IEEE Transactions on Biomedical Engineering, vol. 48, No. 12, Dec. 2001, pp. 1357-1365.

Adair et al., "Biological Effects of Radio-Frequency/Microwave Radiation", IEEE Transactions on Microwave Theory and Techniques, vol. 50, No. 3, Mar. 2002, pp. 953-962.

Emili et al., "Computation of Electromagnetic Field Inside A Tissue At Mobile Communications Frequencies", IEEE Transactions on Microwave Theory and Techniques, vol. 51, No. 1, Jan. 2003, pp. 178-186.

Lin, J., "Noninvasive Microwave Measurement Of Respiration", Proceedings of the IEEE, Oct. 1975, p. 1530.

Lee et al., "Magnetic Gradiometer Based On A High-Transition Temperature Superconducting Quantum Interference Device For Improved Sensitivity Of A Biosensor", Applied Physics Letters, vol. 81, No. 16, Oct. 14, 2002, pp. 3094-3096.

Pedersen et al., "An Investigation Of The Use Of Microwave Radiation For Pulmonary Diagnostics", IEEE Transactions on Biomedical Engineering, Sep. 1976, pp. 410-412.

Chen et al., "An $X$-Band Microwave Life-Detection System", IEEE Transactions on Biomedical Engineering, vol. BME-33, No. 7, Jul. 1986, pp. 697-701.

Lin et al., "Microwave Apexcardiography", IEEE Transactions on Microwave Theory and Techniques, vol. MTT-27, No. 6, Jun. 1979, pp. 618-620.

Rhee, et al., "An Ultra-Low Power, Self-Organizing Wireless Network And Its Applications To Non-Invasive Biomedical Instrumentation", IEEE/Sarnoff Symposium on Advances in Wired and Wireless Communications, Mar. 13, 2002, pp. 64-67.

Prance, et al., "An Ultra-Low-Noise Electrical-Potential Probe For Human-Body Scanning", Meas. Sci. Technol., vol. 11, 2000, pp. 291-297.

Clippingdale et al., "Ultrahigh Impedance Capacitively Coupled Heart Imaging Array", Rev. Sci. Instrum, vol. 65, No. 1, Jan. 1994, pp. 269-270.

Stanley et al., "Pressure-Jump Relaxation Apparatus Using Bipolar-Pulse Conductivity Detection", Rev. Sci. Instrum., vol. 65, No. 1, Jan. 1994, pp. 199-203.

Harland et al., "Electric Potential Probes—New Directions In the Remote Sensing Of The Human Body", Meas. Sci. Technol., vol. 13, 2002, pp. 163-169.

Harland et al., "Remote Detection of Human Electroencephalograms using Ultrahigh Input Impedance Electric Potential Sensors", Applied Physics Letters, vol. 81, No. 17, Oct. 21, 2002, pp. 3284-3286.

Ludwig, H., "Technical Note: Heart- Or Respiration-Rate Calculator", Med. & Biol. Eng. & Comput., vol. 15, 1977, pp. 700-702.

Spinelli et al., "A Novel Fully Differential Biopotential Amplifier With DC Suppression", IEEE Transactions on Biomedical Engineering, vol. 51, No. 8, Aug. 2004, pp. 1444-1448.

Lebedeva, A., "The Use Of Millimeter Wavelength Electromagnetic Waves In Cardiology", Critical Reviews™ in Biomedical Engineering, vol. 28, Nos. 1 and 2, 2000, pp. 339-347.

Taylor et al., "Precision Digital Instrument for Calculation Of Heart Rate and $R$-$R$ Interval", IEEE Transactions On Biomedical Engineering, May 1975, pp. 255-257.

Droitcour et al, "21.1 0.25µm CMOS and BiCMOS Single-Chip Direct-Conversion Doppler Radars For Remote Sensing Of Vital Signs", ISSCC 2002, Session 21, TD: Sensors and Microsystems, Feb. 6, 2002, 2 pgs.

Droitcour et al., "Range Correlation Effect On ISM Band I/Q CMOS Radar For Non-Contact Vital Signs Sensing", IEEE MTT-S Digest, 2003, pp. 1945-1948.

Droitcour et al., "A Microwave Radio For Doppler Radar Sensing Of Vital Signs", undated, 4 pgs.

Hobbie R., "The Electrocardiogram As An Example Of Electrostatics", AJP, vol. 41, Jun. 1973, pp. 824-831.

Hobbie, R., "Improved Explanation Of The Electrocardiogram", Reprinted from American Journal of Physics, vol. 52, 1984, pp. 704-705, Energetics, pp. 234-235.

Liebe, H., "Mini-Review: Atmospheric EHF Window Transparencies Near 35, 90, 140 And 220 GHz", IEEE Transactions On Antennas And Propagation, vol. AP-31, No. 1, Jan. 1983, pp. 127-135.

Byrd, R., "NPO-30697: Non-Contact Electrocardiograph Machine", Opportunity Assessment Prepared for NASA Jet Propulsion Laboratory, Dec. 6, 2002, 40 pgs.

McNamee et al, "Short Communication: No Evidence for Genotoxic Effects from 24 H Exposure Of Human Leukocytes To 1.9 Radiofrequency Fields", Radiation Research, vol. 159, 2003, pp. 693-697.

\* cited by examiner

FIG.6 ELECTRO-STIMULATION TEST SYSTEM

NO STIMULATION

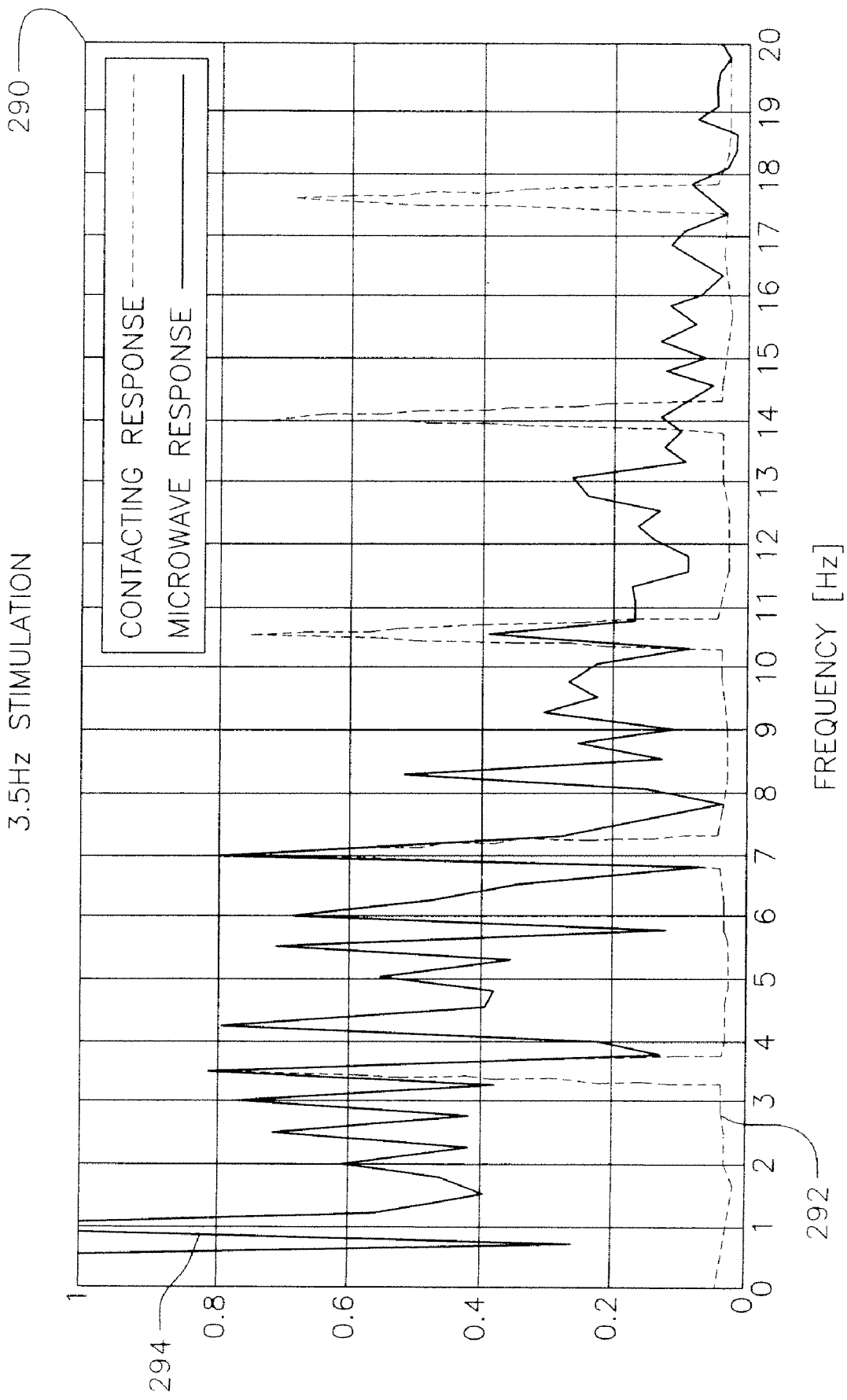

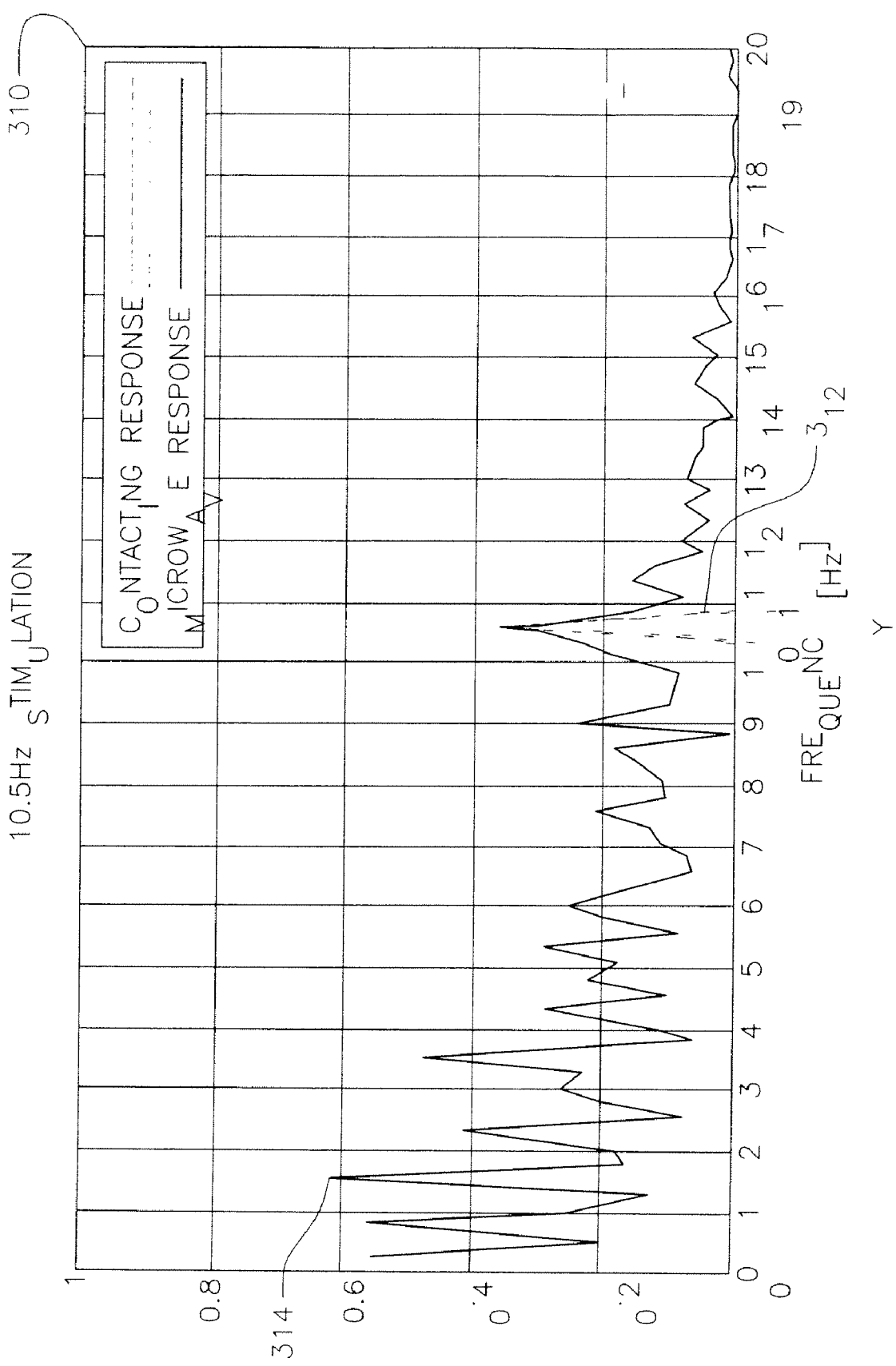

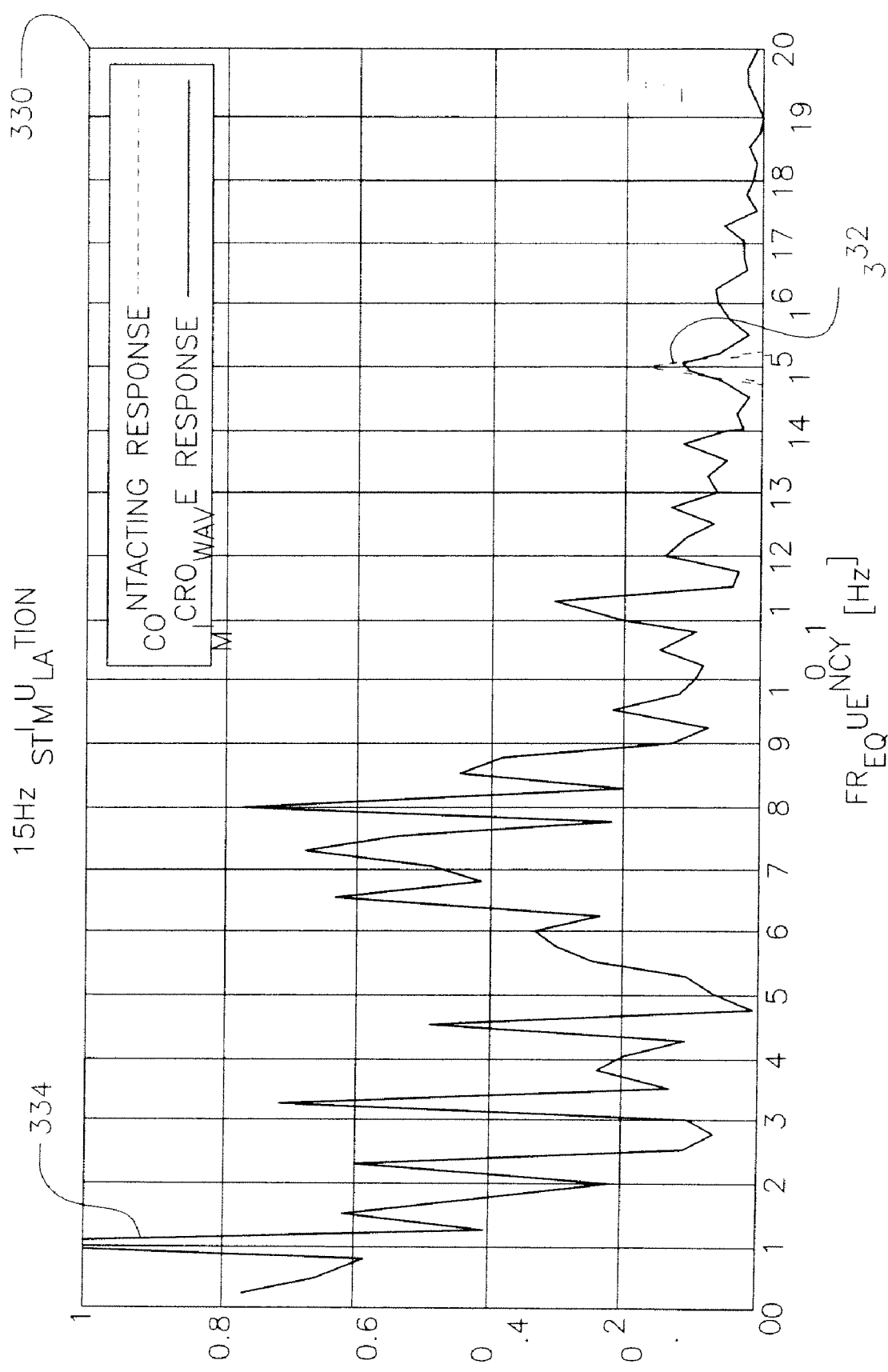

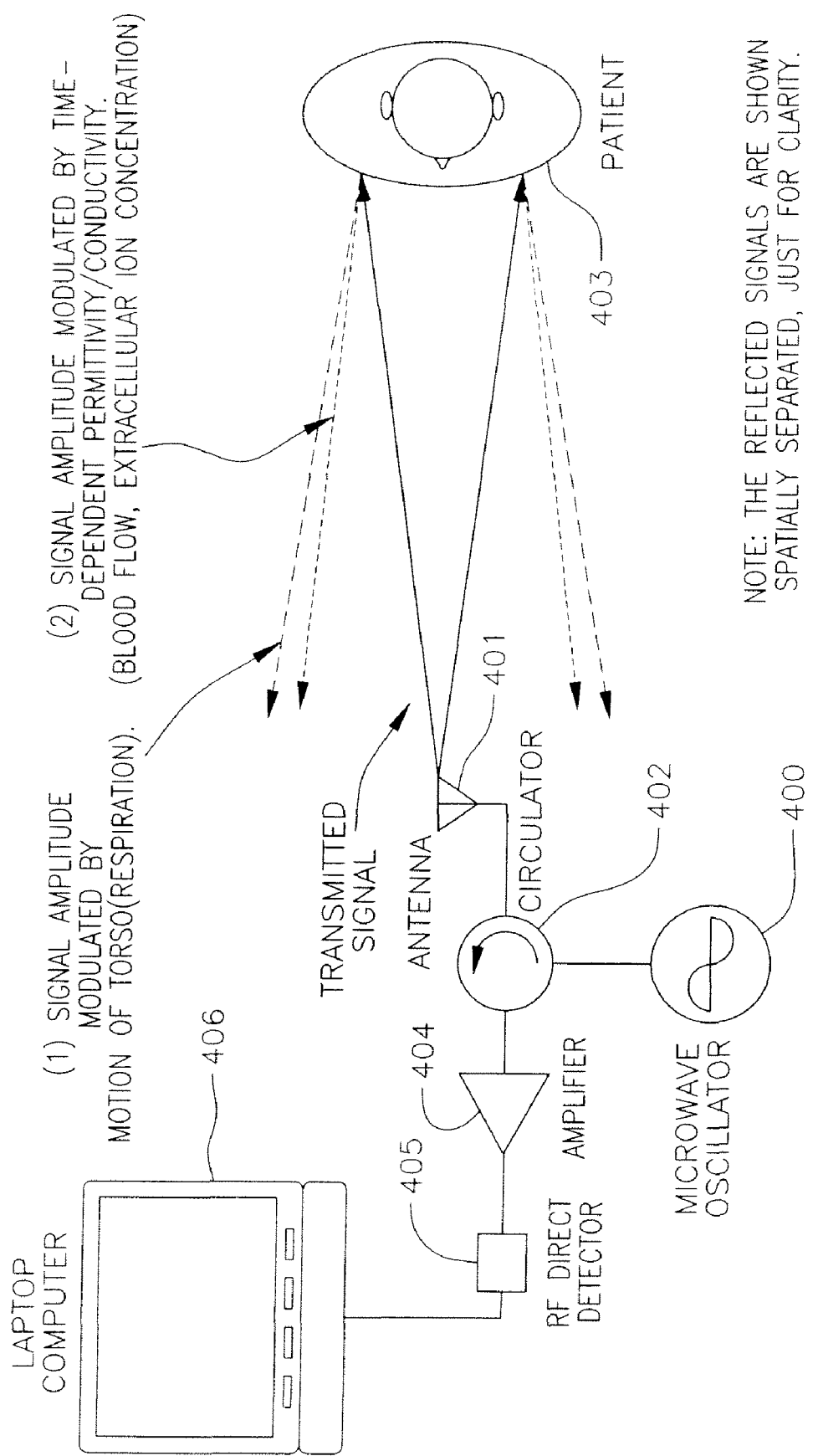

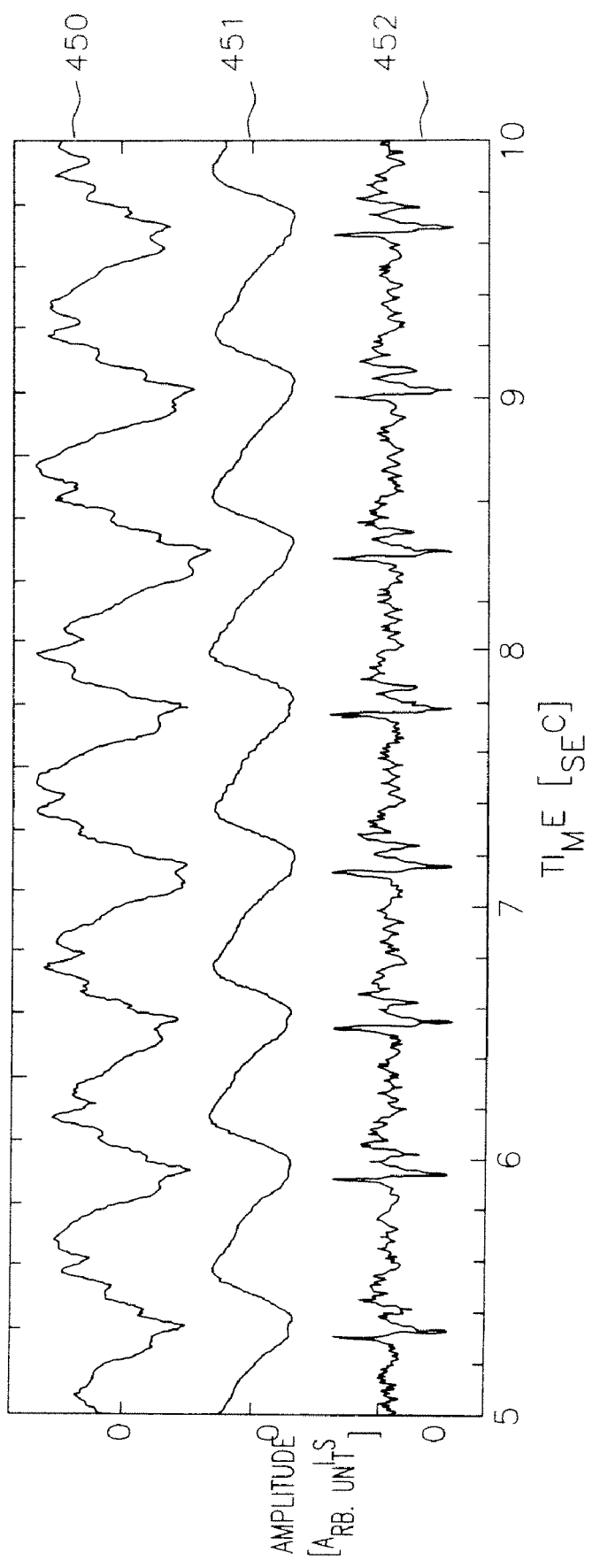

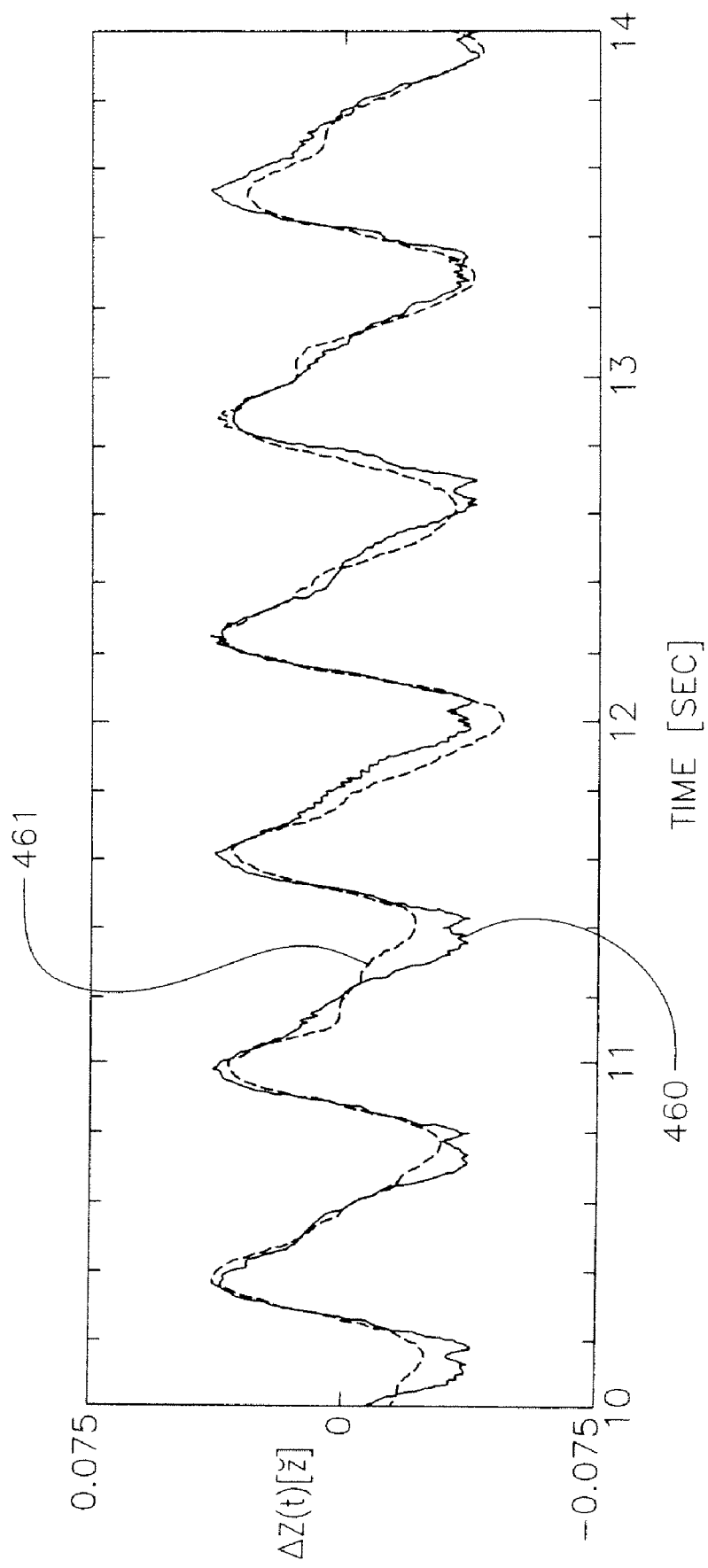

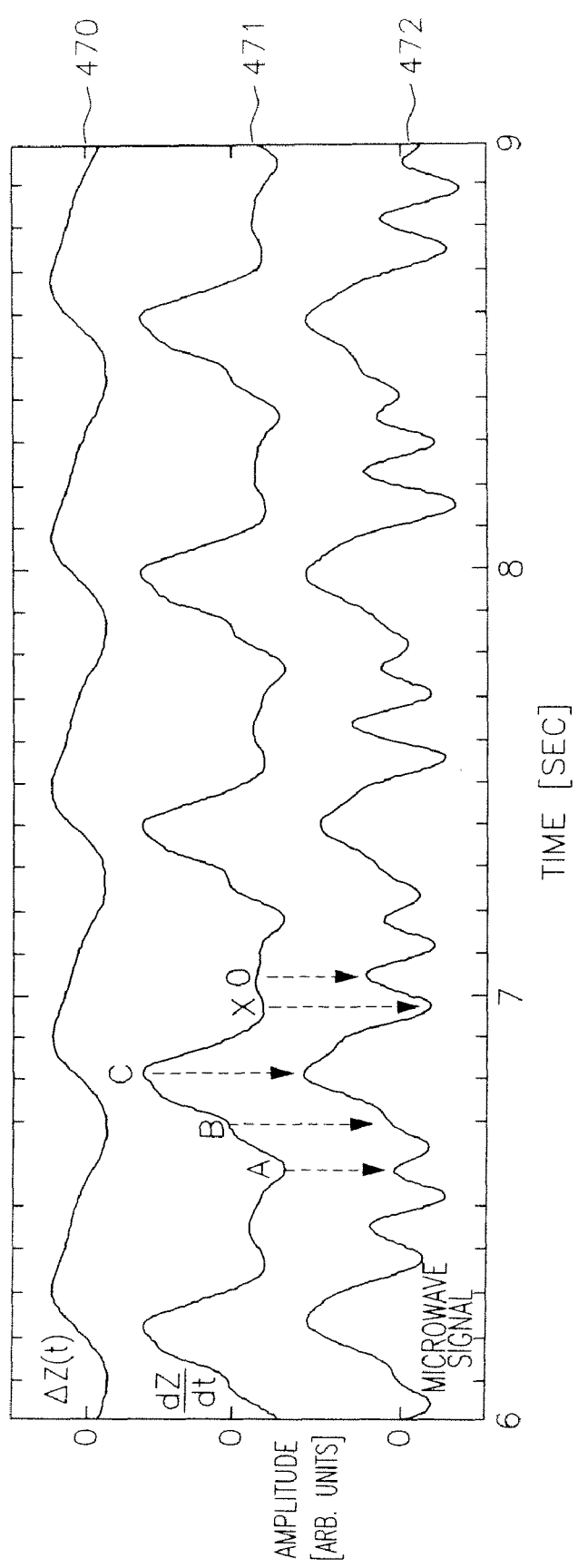

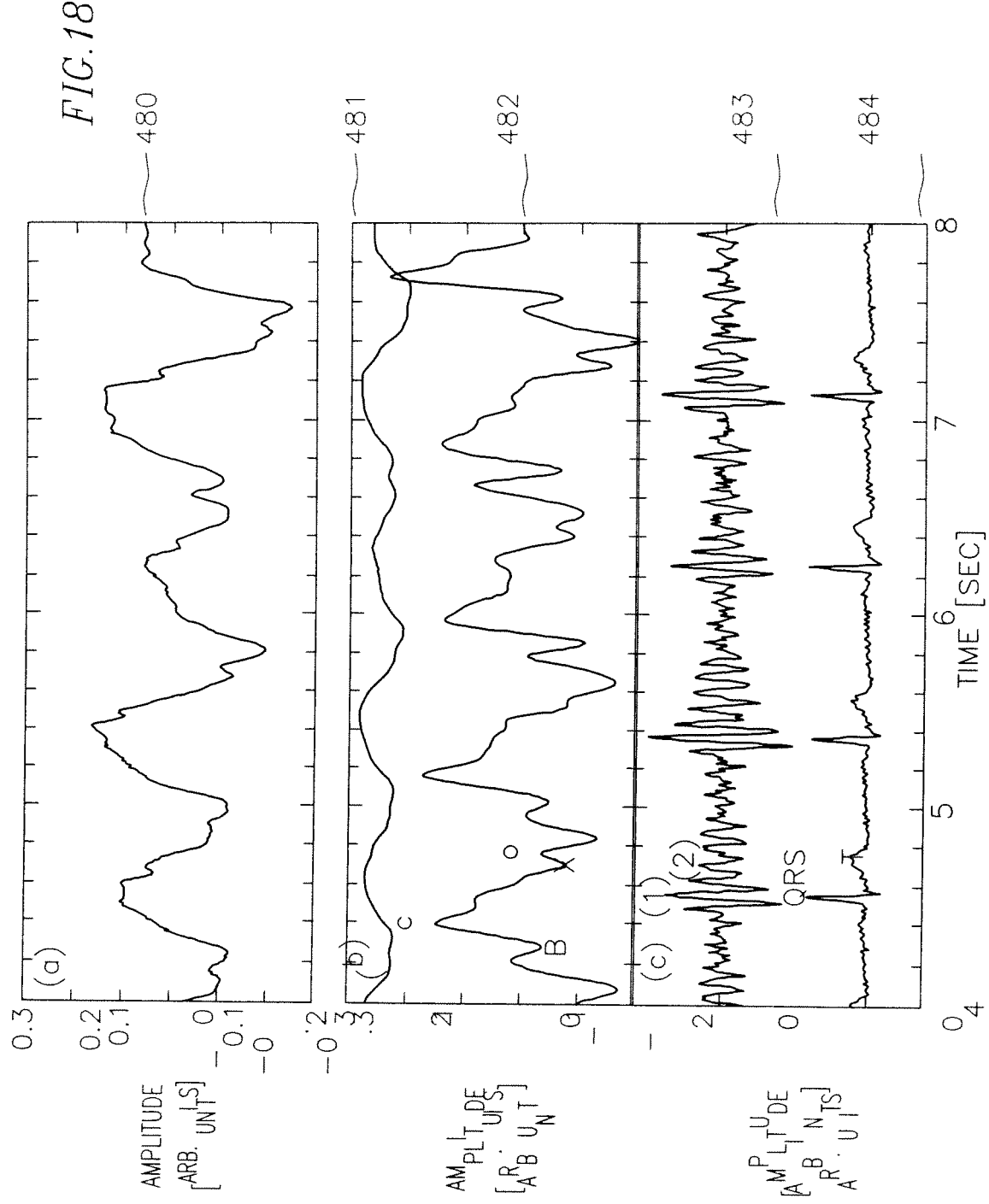

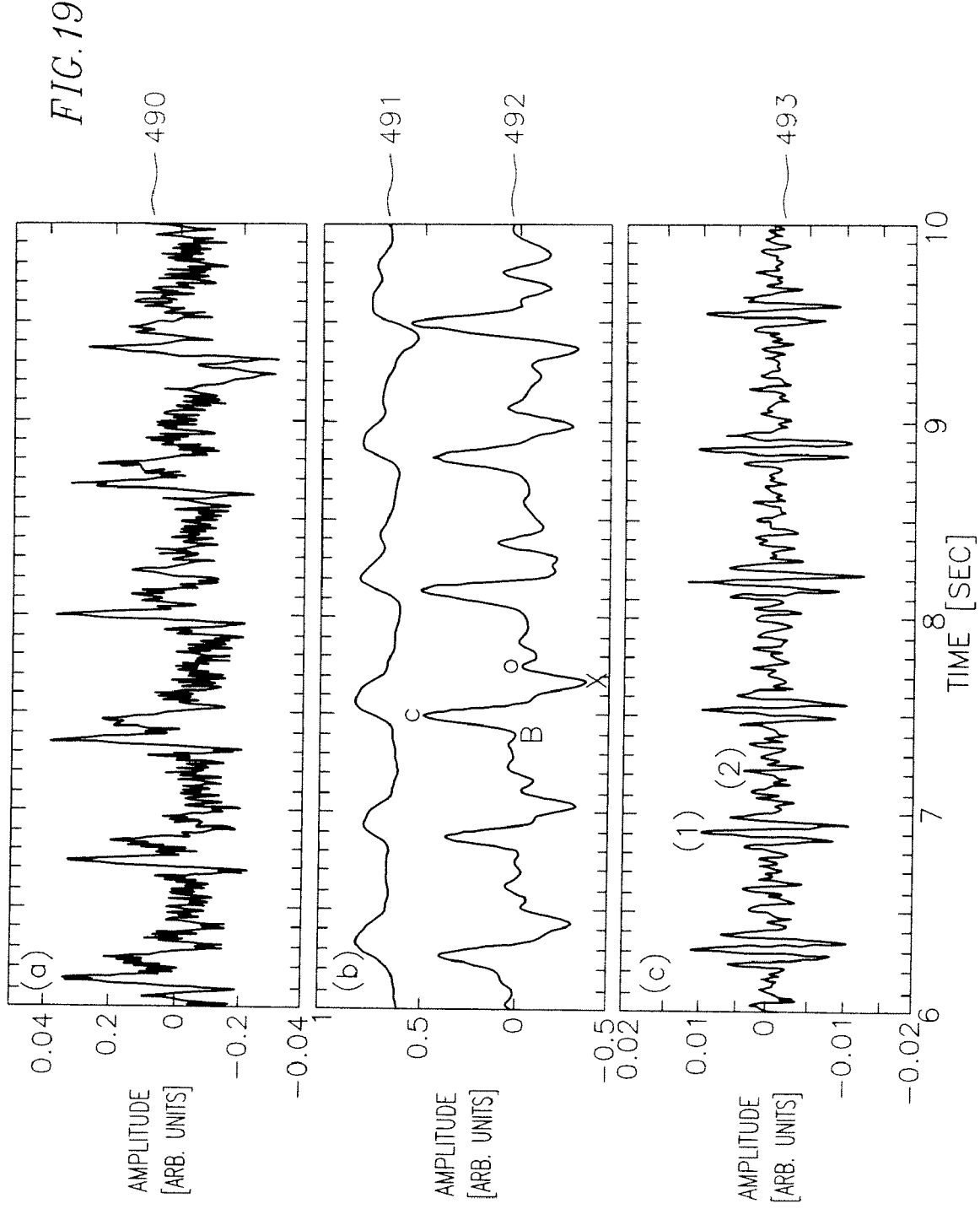

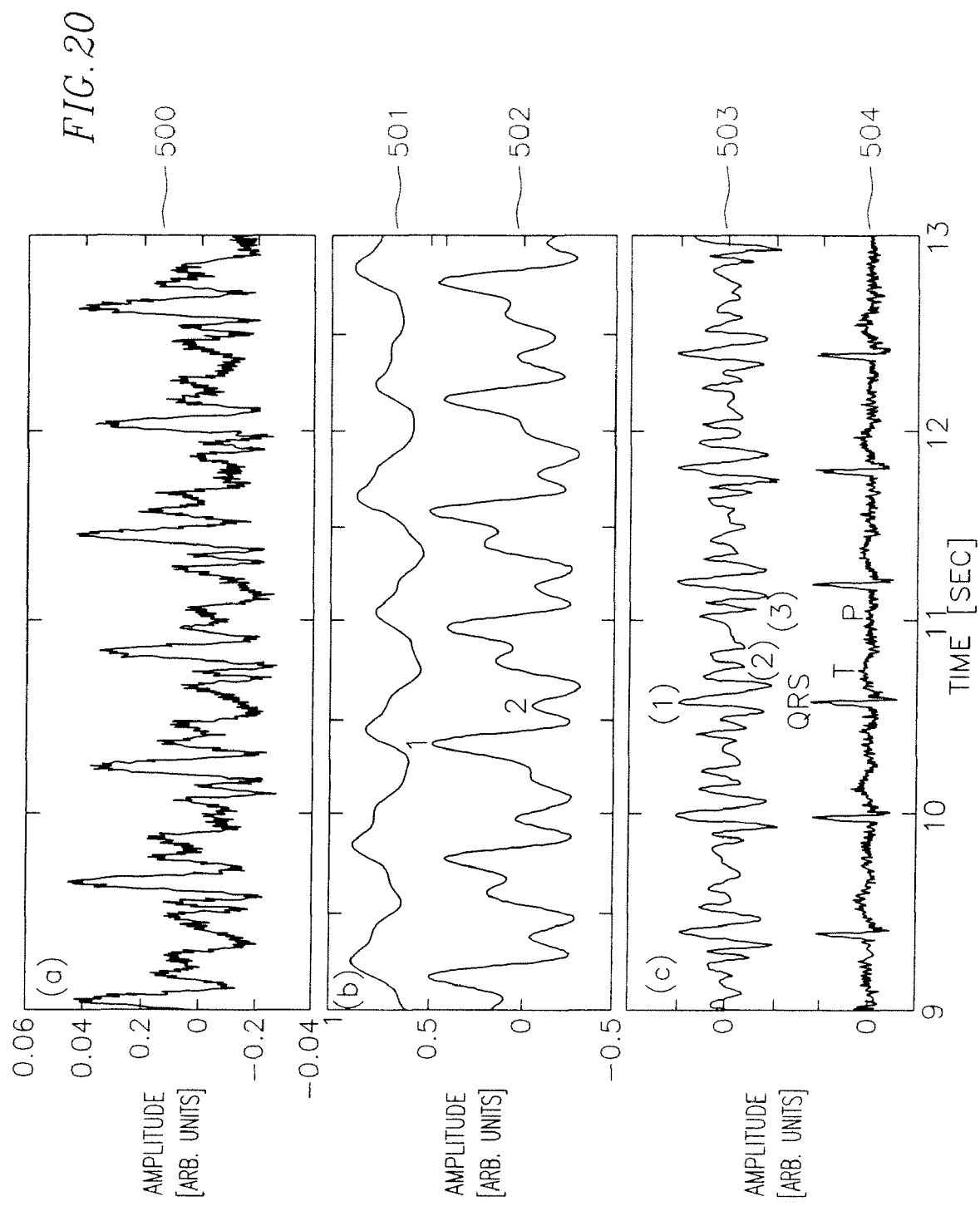

REMOTE-SENSING METHOD AND DEVICE

CROSS-REFERENCE TO RELATED APPLICATION(S)

This application is a continuation-in-part of U.S. application Ser. No. 10/632,347, filed Aug. 1, 2003, now U.S. Pat. No. 7,272,431, which claims the benefit of U.S. Provisional Application No. 60/400,399, filed Aug. 1, 2002, and U.S. Provisional Application No. 60/473,670, filed May 23, 2003, the contents of which are herein incorporated by reference. This continuation-in-part application claims the benefit under 35 U.S.C. 120 of U.S. application Ser. No. 10/632,347 and the benefit under 35 U.S.C. 119(e) of U.S. Provisional Application No. 60/841,765, filed Aug. 31, 2006, the contents of which are herein incorporated by reference.

STATEMENT REGARDING FEDERALLY SPONSORED RESEARCH OR DEVELOPMENT

The U.S. Government has certain rights in this invention pursuant to NAS7-1407 provided by the National Aeronautics and Space Administration, Office of Space Science.

BACKGROUND OF THE INVENTION

1. Field of the Invention

The present invention relates to a remote sensing method and a device, and more particularly, to a remote sensing method and a device utilizing microwaves to remotely measure waveforms directly related to electrocardiographic data, bioimpedance data, phonocardiographic data, and respiration pattern.

2. Description of Related Art

Information concerning a patient's respiration and heart function is vital to the diagnosis and monitoring of many medical conditions. An electrocardiograph is a device that is commonly used to provide information, often in the form of an electrocardiogram, concerning heart function. Electrocardiographs provide outputs that are indicative of electric fields created by the heart as it beats. Operation of an electrocardiograph typically requires attachment of nine leads, which are combined to obtain twelve sets of measurements. A large body of clinical experience has been amassed which has revealed correlations between specific shapes in the waveforms output by an electrocardiograph and many different types of heart conditions.

An impedance cardiograph is another device that is used to provide information, often in the form of an impedance cardiogram, concerning heart function. Impedance cardiographs measure changes in impedance within tissue to estimate changes in volume of a patient's body and organs. In several systems, alternating currents are transmitted through a patient's chest. The current seeks the path of least resistance, which theory predicts to be the blood filled aorta. As blood volume and velocity in the aorta change with each heartbeat, so too does the impedance of the tissue in the patient's chest. The changes in impedance can be used for diagnostic purposes.

Sounds made by the heart as it beats are the most commonly used indicator of basic heart function. A physician typically listens for the normal first, S1, and second, S2, heart sounds using a stethoscope pressed against the patient's chest. If sounds in addition to S1 and S2 are heard, such as a so-called "heart murmur," these sounds indicate that further tests are necessary to assess the condition of the patient's heart. Such additional sounds should not normally be present, and can indicate a variety of abnormal heart conditions, such as a leaky heart valve, for example. A phonocardiograph is a device commonly used to provide detailed information on heart sounds, usually in the form of a phonocardiogram. The phonocardiogram waveform is measured by placing a sensitive microphone, or accelerometer, in contact with the chest at one of several well-defined auscultation locations. There is a large body of clinical data to assist in interpreting the phonocardiogram for diagnostic purposes, such as, for example, Rangaraj M. Rangayyan and Richard J. Lehner, "Phonocardiogram signal analysis", CRC Critical Reviews in Biomedical Engineering, vol. 15, issue 3, pp. 211-236 (1998), which is herein incorporated by reference.

Electrocardiographs and impedance cardiographs typically involve attaching electrical leads to the subject being measured, and impedance cardiographs typically involve passing a current through the subject's body. Phonocardiographs require attaching a specially-designed microphone or accelerometer to the subject's torso.

U.S. Pat. Nos. 6,122,537; 5,760,687; 4,958,638; 6,753,780; 6,208,286; 6,031,482; and 5,488,501, which are herein incorporated by reference, demonstrate modulation of the phase and/or frequency of a reflected microwave signal (i.e., radar or Doppler radar techniques) to provide a measurement of pulse rate and/or respiration rate.

SUMMARY OF THE INVENTION

A remote-detection system is provided for monitoring changes in permittivity associated with physiological activity of a subject that is free to move. The system includes a source containing an oscillator configured to illuminate tissue of the subject with an electromagnetic signal beam. The system further includes a receiver configured to receive reflections of the electromagnetic signal beam from the subject. The reflections include amplitude variations indicative of motion of the illuminated tissue and amplitude variations indicative of time dependent variations in the permittivity of the illuminated tissue associated with electrical activity of the subject's heart. The system further includes a detector connected to the receiver and configured to extract from the reflected signal beam the variations in amplitude indicative of motion of the illuminated tissue or indicative of time dependent variations in the permittivity of the illuminated tissue associated with the electrical activity of the subject's heart.

In an exemplary embodiment of the present invention, the detector is configured to extract from the reflected signal beam the variations in amplitude indicative of motion of the illuminated tissue as correlates with heart sounds or a phonocardiogram of the subject.

In an exemplary embodiment of the present invention, the source also includes a first antenna portion, and the receiver includes a second antenna portion connected to the detector.

In an exemplary embodiment of the present invention, the source and the receiver are directionally coupled to a single antenna that acts as the first antenna portion and the second antenna portion.

In an exemplary embodiment of the present invention, the subject has a beating heart; the permittivity of the illuminated tissue changes in response to the beating heart; the amplitude of the reflected electromagnetic signal beam changes as the permittivity of the illuminated tissue changes; and the detector is configured to extract from the reflected electromagnetic signal beam variations in amplitude associated with the changes in the permittivity of the illuminated tissue.

A remote-detection system is provided for monitoring the physiological activity of a subject. The system includes means for illuminating tissue of the subject with an electromagnetic signal. The system further includes means for detecting reflections of the electromagnetic signal. The reflections include amplitude variations indicative of motion of the illuminated tissue and amplitude variations indicative of time dependent variations in the permittivity of the illuminated tissue associated with electrical activity of the subject's heart. The system further includes means for extracting a signal indicative of the changes in the amplitude of the electromagnetic signal reflected by the illuminated tissue that are associated with motion of the illuminated tissue or with time dependent changes in the permittivity of the illuminated tissue associated with the electrical activity of the subject's heart.

In an exemplary embodiment of the present invention, the system further includes means for extracting a signal indicative of the changes in the amplitude of the electromagnetic signal reflected by the illuminated tissue that are associated with motion of the illuminated tissue as correlates with heart sounds or a phonocardiogram of the subject.

A method of observing changes in the permittivity of a subject associated with physiological activity is provided. Tissue of the subject is illuminated with an electromagnetic signal beam. Reflections of the electromagnetic signal beam are received that include amplitude variations indicative of motion of the illuminated tissue and amplitude variations indicative of time dependent variations in the permittivity of the illuminated tissue associated with electrical activity of the subject's heart. From the reflected signal a signal is extracted indicative of the changes in the amplitude of the electromagnetic signal associated with motion of the illuminated tissue or with time dependent changes in the permittivity of the illuminated tissue associated with the electrical activity of the subject's heart.

In an exemplary embodiment of the present invention, from the reflected signal a signal is extracted indicative of the changes in the amplitude of the electromagnetic signal associated with motion of the illuminated tissue as correlates with heart sounds or a phonocardiogram of the subject.

A remote sensing system and method are provided for providing physiological data of a subject. The system includes a transmitter, a receiver, and a processor. The transmitter is for transmitting a microwave signal to illuminate tissue of the subject. The receiver is for receiving a reflected microwave signal. The reflected microwave signal is a reflection of the microwave signal from illuminated tissue of the subject. The processor is for processing the reflected microwave signal. The processor is configured to analyze an amplitude of the reflected microwave signal to determine changes in permittivity of the illuminated tissue of the subject. The changes in permittivity contain a DC component and a time-varying component. The processor is configured to process the time-varying component to provide cardiographic related data of the subject.

In an exemplary embodiment of the present invention, the cardiographic related data correlate with an electrocardiogram or an impedance cardiogram.

In an exemplary embodiment of the present invention, the processor is further configured to process the time-varying component to provide a respiratory pattern and/or a pulse rate of the subject.

In an exemplary embodiment of the present invention, the transmitter includes an RF oscillator coupled to a circulator and an antenna coupled to the circulator. In addition, the receiver includes the antenna coupled to the circulator. Furthermore, the processor includes an amplifier, a direct detector, and a computer.

In an exemplary embodiment of the present invention, the microwave signal has a frequency between 100 MHz and 200 GHz.

BRIEF DESCRIPTION OF THE DRAWINGS

FIG. 8 is a frequency-domain graph showing the response measured by a system in contact with the subject and the response measured by a remote-detection system in accordance with the present invention when an external stimulation signal of 3.5 Hertz is applied to the arm of the subject.

FIG. 9A is a frequency-domain graph showing the response measured by a system in contact with the subject and the response measured by a remote-detection system in accordance with the present invention when an external stimulation signal of 10.5 Hertz is applied to the arm of the subject.

FIG. 9B is a frequency-domain graph showing the response measured by a system in contact with the subject and the response measured by a remote-detection system in accordance with the present invention when an external stimulation signal of 15 Hertz is applied to the arm of the subject.

FIG. 10 is a schematic view of a remote-detection system in accordance with another embodiment of the present invention illuminating a subject with an electromagnetic signal. For clarity only, motion and permittivity information carrying components of the reflected signal are shown spatially separated.

FIG. 15 is a graph showing an ICG waveform that shows a characteristic steep rise due to the ventricular systole and shows a lowpass-filtered microwave cardiogram with adjusted amplitude to match the ICG waveform.

FIG. 16 is a graph showing an ICG measured with contacting electrodes, the derivative of the ICG including points indicating the A-wave (atrial systole), the C-wave (ventricular systole), the O-wave (ventricular diastole), and the points B and X (aortic valve opening and closing, respectively), and the derivative of the lowpass-filtered microwave cardiogram with vertical dashed lines indicating significant similarities between the waveforms. The vertical scale for each curve was adjusted to allow the three curves to be shown together.

FIG. 19 is a graph showing (a) microwave cardiogram measured for an adult male located behind an interior wall; (b) the lowpass filtered microwave cardiogram and its derivative with the A-wave, O-wave, C-wave, and the X and B points identified; and (c) the highpass filtered microwave cardiogram.

FIG. 20 is a graph showing (a) microwave signal reflected from the lower abdomen; (b) the lowpass filtered microwave signal and its derivative; and (c) the highpassed-filtered microwave cardiogram and the unfiltered ECG.

DETAILED DESCRIPTION

Figure 1:
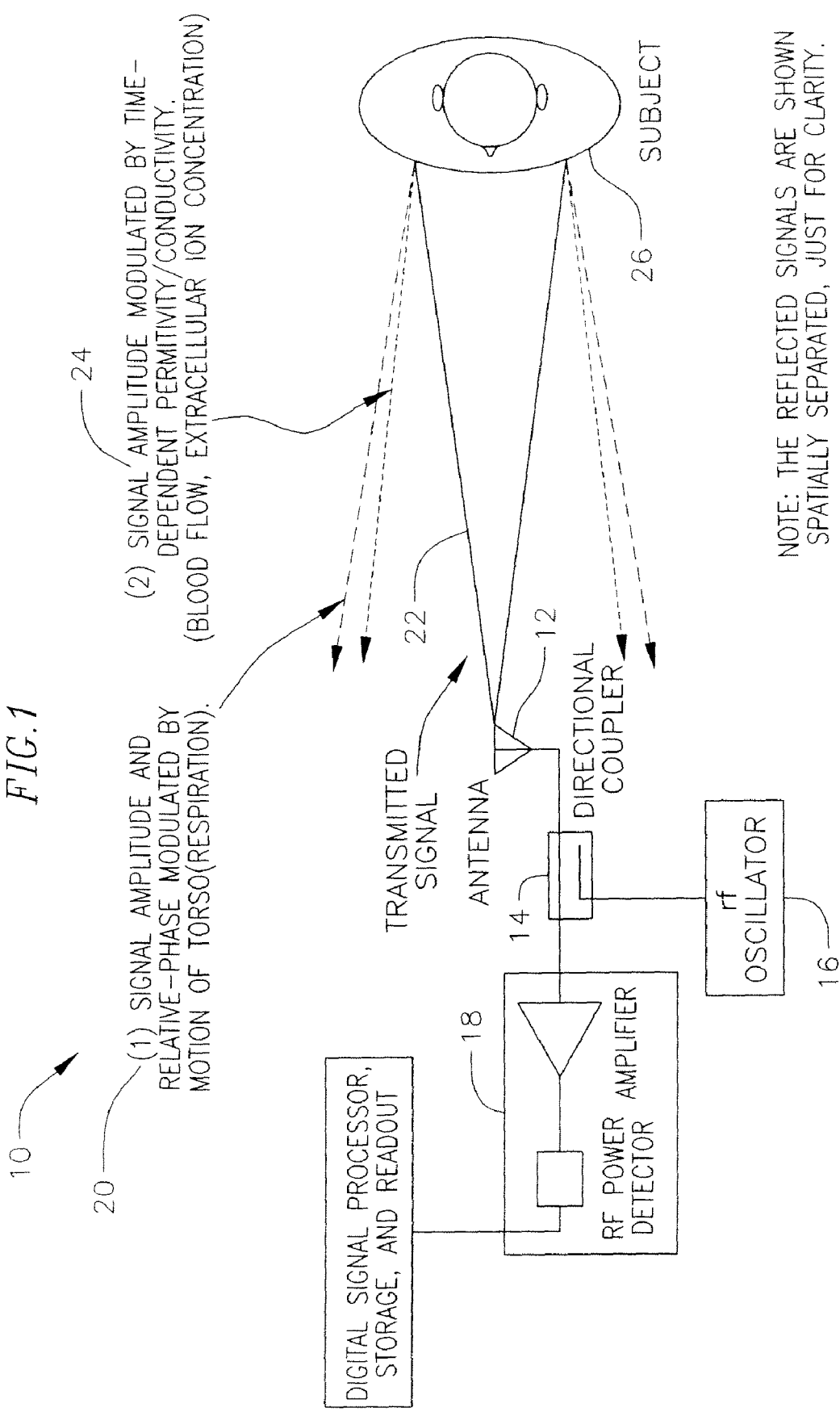
FIG. 1 is a schematic view of a remote-detection system in accordance with an embodiment of the present invention illuminating a subject with an electromagnetic signal. For clarity only, motion and permittivity information carrying components of the reflected signal are shown spatially separated.

Embodiments of the present invention use reflected electromagnetic signals to observe respiration and pulse and to generate a phonocardiographic-related waveform, an impedance-cardiographic-related waveform, and an electrocardiographic-related waveform of a subject. Remote-detection systems in accordance with the present invention typically work by using an RF oscillator to generate an electromagnetic signal beam that is then used to illuminate tissue on a portion of a subject. In operation, the subject's respiration and changes in the dielectric value or permittivity, $\epsilon$, of a patient's body tissue accompanying each heartbeat can contribute to correlated variations in the reflection-coefficient at the air-tissue interface of the electromagnetic signal reflected by the subject, and thus directly changing the amplitude of the reflected signal. An output indicative of the amplitude of the reflection-coefficient which directly effects the amplitude of the signal reflected by the subject is generated. Digital signal processing techniques can be performed to extract the portions of the output that are indicative of the respiration rate and/or the pulse rate that produce information analogous to an electrocardiogram, an impedance cardiogram, or a phonocardiogram of the subject.

In one embodiment adapted for monitoring the physiological activity of a subject, the invention includes a source containing an oscillator configured to illuminate a subject with an electromagnetic beam and a receiver configured and optimized to observe changes in the amplitude of the electromagnetic beam reflected by the subject. The receiver is also responsive to the phase of the reflected signal, due to the small leakage, present in all real RF systems, of the source signal into the receiver. In all the prior art which uses an electromagnetic beam to obtain physiologic or cardiographic information on a subject, it is always assumed that the human body represents a dielectric with a fixed (i.e., not time-dependent) dielectric constant or permittivity. This average constant value is well-documented in the open literature. Variations in the reflected signal, as measured by the prior art embodiments, are taken to be due to mechanical, or motion-related, changes in the illuminated area of the subject, which are always assumed to be best measured by optimized observations (usually based on homodyne-detection techniques) of the phase of the reflected signal while ignoring, or intentionally clipping off, the changes in amplitude of the reflected signal. The invention described here takes a fundamentally different approach. In this approach, it is realized that while the human body does indeed have a large static, or basal, average permittivity, there are also extremely-small time-dependent variations in the permittivity which are driven by, and thus synchronous with, the beating heart. These periodic time-dependent variations in the permittivity primarily modulate the amplitude of the reflected signal by changing the actual value of the reflection coefficient of the electromagnetic wave at the surface of the body. This is in contrast to all prior art, which takes the reflection coefficient at the surface of the body tissue to be a fixed value, which is determined by the large average static-value of the permittivity or dielectric constant. In the embodiment of the invention disclosed here as mentioned above, the receiver is optimized to respond to the amplitude of the reflected electromagnetic waves, thus allowing measurements of cardiac function related to the electrical nature of the heart. This allows for measurements of waveforms related to the electrocardiographic and impedance-cardiographic physiology of the subject. In addition, since the receiver is also responsive (though intentionally unoptimized) to phase (as any receiver made from real-world components would be), motion related effects can also be measured. In a further embodiment, when operated at very high frequency, greater than about 10 GHz, it is possible to measure the actual waveform of the heart sounds, which cause extremely small amplitude vibrations at the surface of the body; such heart-sound waveforms are commonly referred to as the phonocardiogram of a subject.

Turning now to the diagrams, FIG. 1 illustrates a remote-detection system 10 in accordance with the present invention that includes an antenna 12 coupled via a directional coupler 14 to an RF oscillator 16 and an amplifier and RF power detector 18. In addition, the RF detector is connected to a digital signal processor 20. The RF oscillator and the antenna can illuminate a subject 24 with an electromagnetic beam 22. The subject typically reflects a portion of the incident electromagnetic signal and the antenna and the RF detector can be used to generate a signal indicative of the amplitude of the reflected signal. Information can then be extracted from the signal generated by the antenna and the RF detector by the digital signal processor 20.

When a subject is illuminated with an electromagnetic signal generated by a remote-detection system 10 in accordance with the present invention, the electromagnetic signal can be reflected as a result of the signal encountering a boundary between materials having different complex permittivity values. In the illustrated embodiment, the subject is a human and the electromagnetic signal beam 22 illuminates the subject's torso 26. Air has a dielectric constant near 1, which is very low compared to the permittivity of human tissue, which is a complex function of frequency, temperature, and ion-concentration. Therefore, a significant amount of any electromagnetic signal illuminating a human subject will be reflected by the subject's body. The amplitude and pattern of the reflected signal can depend at least in part on changes in the permittivity of the illuminated tissue of the subject. The permittivity of a material may change with a change in the composition and/or configuration of ions, and/or their mobilities, in the material, or changes in the fluid-content or chemical composition of the material. Thus, the amplitude and pattern of the reflected signal often depends at least partially on the shape and/or configuration of the subject's body, as well as the water and ion content of the tissues. These permittivity changes can be associated with the depolarization waves that sweep the heart as it beats, or with changes in the location of blood volumes within the body as the heart pumps. These and other physiological processes therefore can alter the pattern of the reflected signal in ways that can be observed using the antenna. Changes also occur in the shape or position of a subject's chest (i.e., mechanical changes) or structures inside the chest that are associated with respiration. These mechanical changes also alter the parameters of the reflected signal.

Figure 2:
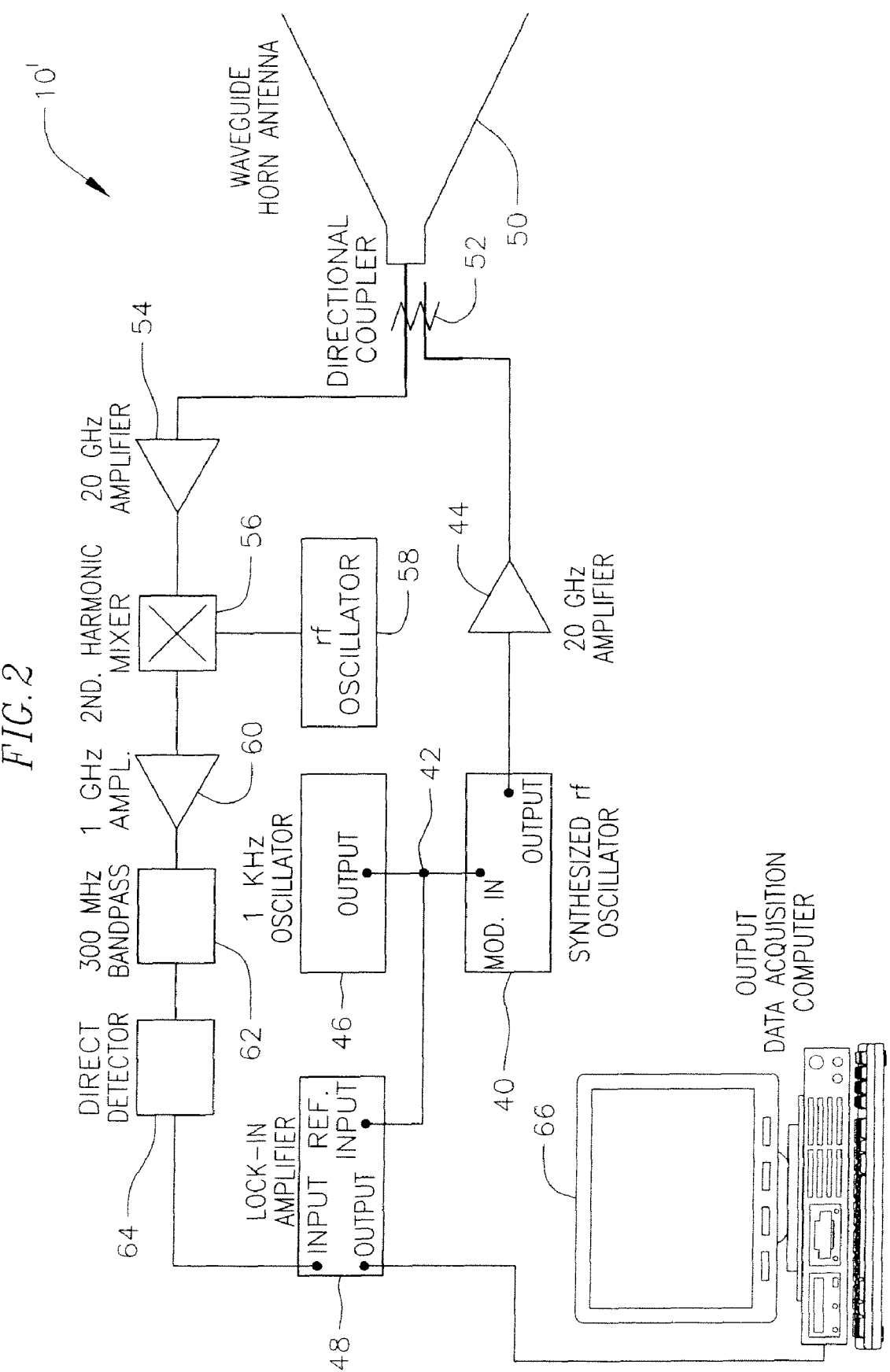
FIG. 2 is a block diagram of the components of a system in accordance with an embodiment of the present invention.

A block diagram of a remote-detection system in accordance with the present invention is illustrated in FIG. 2. The remote-detection system 10' includes a synthesized RF oscillator 40 that is connected to a common node 42 and a first amplifier 44. The common node 42 is connected to an oscillator 46 and a lock-in amplifier 48. The output of the first amplifier 44 is connected to an antenna 50 via a directional coupler 52. The directional coupler is also connected to a second amplifier 54. The output of the second amplifier is connected to a mixer 56. A separate RF oscillator 58 provides an output to the mixer. This is a heterodyne technique which allows the high microwave frequency to be shifted down to a lower RF frequency, while preserving amplitude information, where a narrow bandpass or lowpass filter can then be employed to reduce the overall noise of the system. (Note that this is not the same as the homodyne technique of frequency conversion used in Doppler, and other types of Radars.) The output of the mixer is connected to the input of a third amplifier 60. The output of the third amplifier is connected to a bandpass filter 62 and the output of the bandpass filter is connected to a direct detector 64 of RF power. An output of the RF direct detector 64 is connected to an input of the lock-in amplifier 48 and the output of the lock-in amplifier 48 is then provided to a data acquisition computer 66. This scheme using a mixer and lock-in amplifier allows the noise of the system to be reduced, thus improving the overall signal-to-noise ratio, but it is not fundamentally required for the detection of the cardiographic-related signals.

In one embodiment, the synthesized RF oscillator 40 produces an electromagnetic signal in the range of 20 GHz and can be implemented using a Model 33120A manufactured by Hewlett-Packard Company of Palo Alto, Calif. ("Hewlett-Packard"). The amplitude of the signal is modulated by a 1-to-10 kilohertz range signal generated by oscillator 46 which is implemented using a Model 83723B manufactured by Hewlett-Packard. The first amplifier 44 boosts the strength of the signal and is implemented using a 2-20 GHz amplifier such as a Model 8349B manufactured by Hewlett-Packard. The waveguide horn antenna 50 produces the radiated signal beam and is implemented using a Model 639 manufactured by the Narda division of L-3 Communications Corporation of New York, N.Y. The directional coupler 52 couples the signal to be radiated to the antenna 50 and the signal received by the antenna 50 to second amplifier 54, and is implemented using a Model P752C-10 dB manufactured by Hewlett-Packard. The second amplifier 54 provides a low-noise amplification of the reflected signal and is implemented using a 20 GHz amplifier such as a Model AMF-3D-000118000-33-10P manufactured by MITEQ, Inc. of Hauppauge, N.Y. ("MITEQ"). The 2nd harmonic mixer 56 down-converts the signal to 1 GHz and can be implemented using a Model SBE0440LWI manufactured by MITEQ. The RF oscillator 58 serves as the local oscillator for the mixer 56 and is implemented using a Model 8340A manufactured by Hewlett-Packard. The third amplifier 60 boosts the signal to a level appropriate for the direct detector 64 and can be implemented using a 1 GHz amplifier such as a Model 4D-00011800-33-10P manufactured by MITEQ. The bandpass filter 62 limits the signal reception bandwidth in order to reduce the noise of the detection system and can be implemented using a 300 MHz bandpass filter such as a Model 381-1390-50S11 manufactured by Reactel, Incorporated of Gaithersburg, Md. The direct detector 64 produces a video response proportional to the amplitude of the reflected electromagnetic signal and can be implemented using a Model 8473C manufactured by Hewlett-Packard. The lock-in amplifier 48 detects the amplitude of the output from the direct detector 64 synchronously with the 1-to-10 kilohertz range modulation signal generated by oscillator 46, and can be implemented using a Model SR830 manufactured by Stanford Research Systems of Sunnyvale, Calif. ("Stanford Research Systems"). The data acquisition computer 66 digitizes the output of the lock-in amplifier 48, stores the signal, and displays the signal in a graphical format. The computer 66 may be implemented using a Macintosh Model 8600/300 manufactured by Apple Computer, Inc. of Cupertino, Calif. (an "Apple Macintosh").

The heart generates an electric field as a result of a portion of the heart being polarized and a portion of the heart being depolarized. When the heart beats, heart cells are thought to be initially polarized due to an imbalance in the concentration of ions on either side of cell membranes. As the heart muscles contract, the cell membranes of the heart muscle cells are thought to become permeable and the concentration of ions on either side of the membrane balances. Observations indicate that heart muscle cells do not depolarize simultaneously. Rather, a depolarization wave sweeps across the heart starting in the atria and moving to the ventricles. Once the heart has finished contracting, the heart muscle cells repolarize. The depolarization and repolarization of the various portions of the heart act as dipole-like current generators which drive ionic currents, primarily Cl⁻ and Na⁺ ions, in the extra-cellular fluid in bodily tissues. These ionic currents are proportional to the electric dipole fields generated by the heart. The ionic currents can be converted to conventional electron currents using Ag/AgCl electrodes placed in contact with the body, and amplified and detected for further study. The resulting waveforms obtained this way are commonly referred to electrocardiograms, and are indicative of the dipole moment, and can be used in medical diagnosis.

Figure 3:
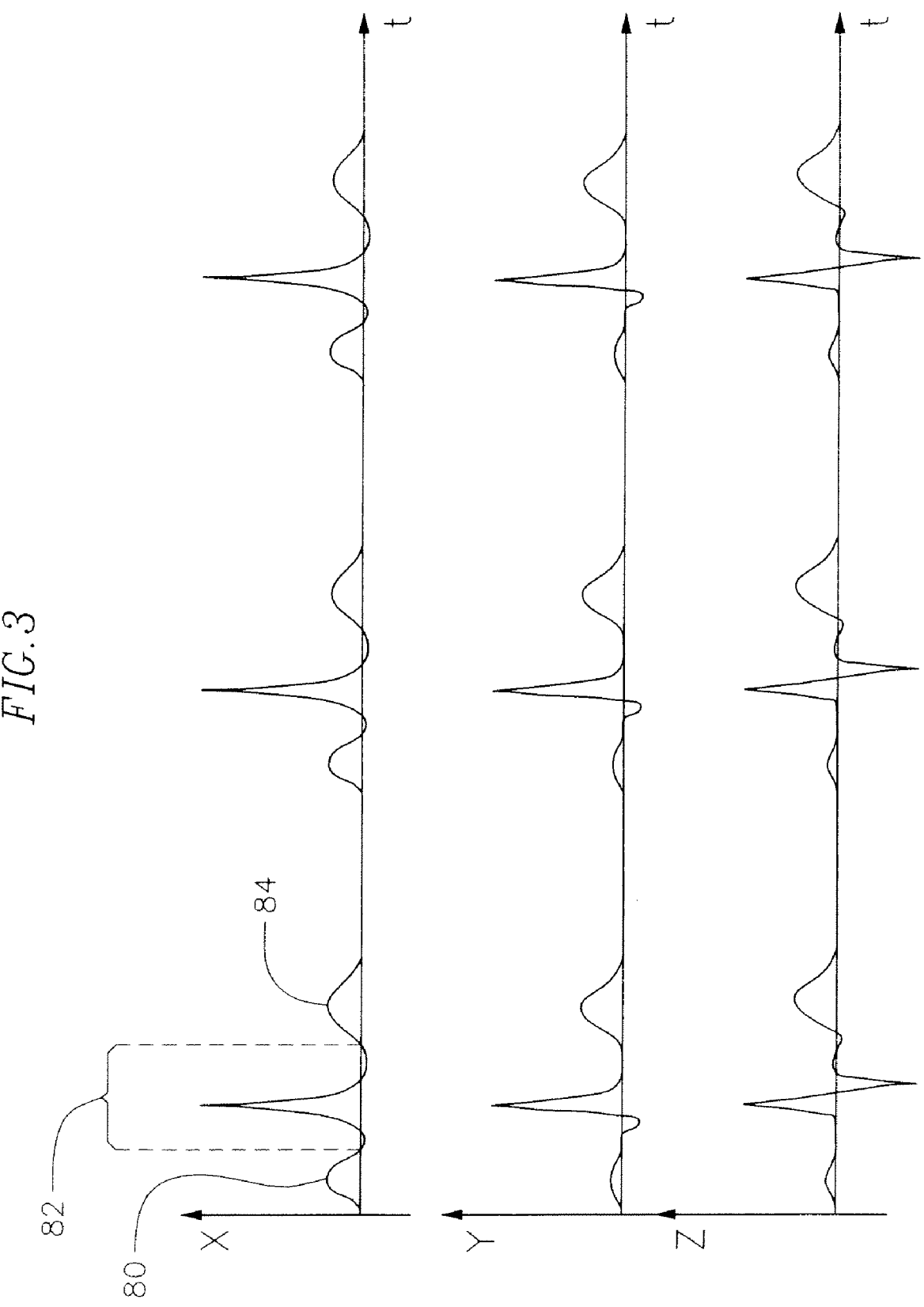
FIG. 3 is a schematic illustration of three orthogonal components of the dipole of a heart during depolarization and repolarization.

FIG. 3 shows an example of the orthogonal components of the dipole moment generated by a heart during three successive beats. The magnitude of the orthogonal components of the electric field during the P wave (80), the QRS complex (82) and the T wave (84) are indicated on the graph, which depicts the x, y, and z-components of the dipole moment. The changes in strength and direction of the dipole moment of the heart provides information concerning the electrophysiology of the heart. Theory predicts that the dipole generated by the heart during the depolarization of the atria generates a P-wave on the output of an electrocardiograph. Theory also predicts that the dipole of the heart during the depolarization of the ventricles generates a series of waves on the output of an electrocardiograph known as the "QRS complex." The T-wave is thought to be associated with the dipole generated by the heart during repolarization of the ventricles. A further description of the electric field and physiology of the heart as it beats is provided in the paper published by R. K. Hobbie in the American Journal of Physics, vol. 41, p. 824 (1973) entitled "The Electrocardiogram as an Example of Electrostatics," which is incorporated herein by reference in its entirety.

Figure 4:
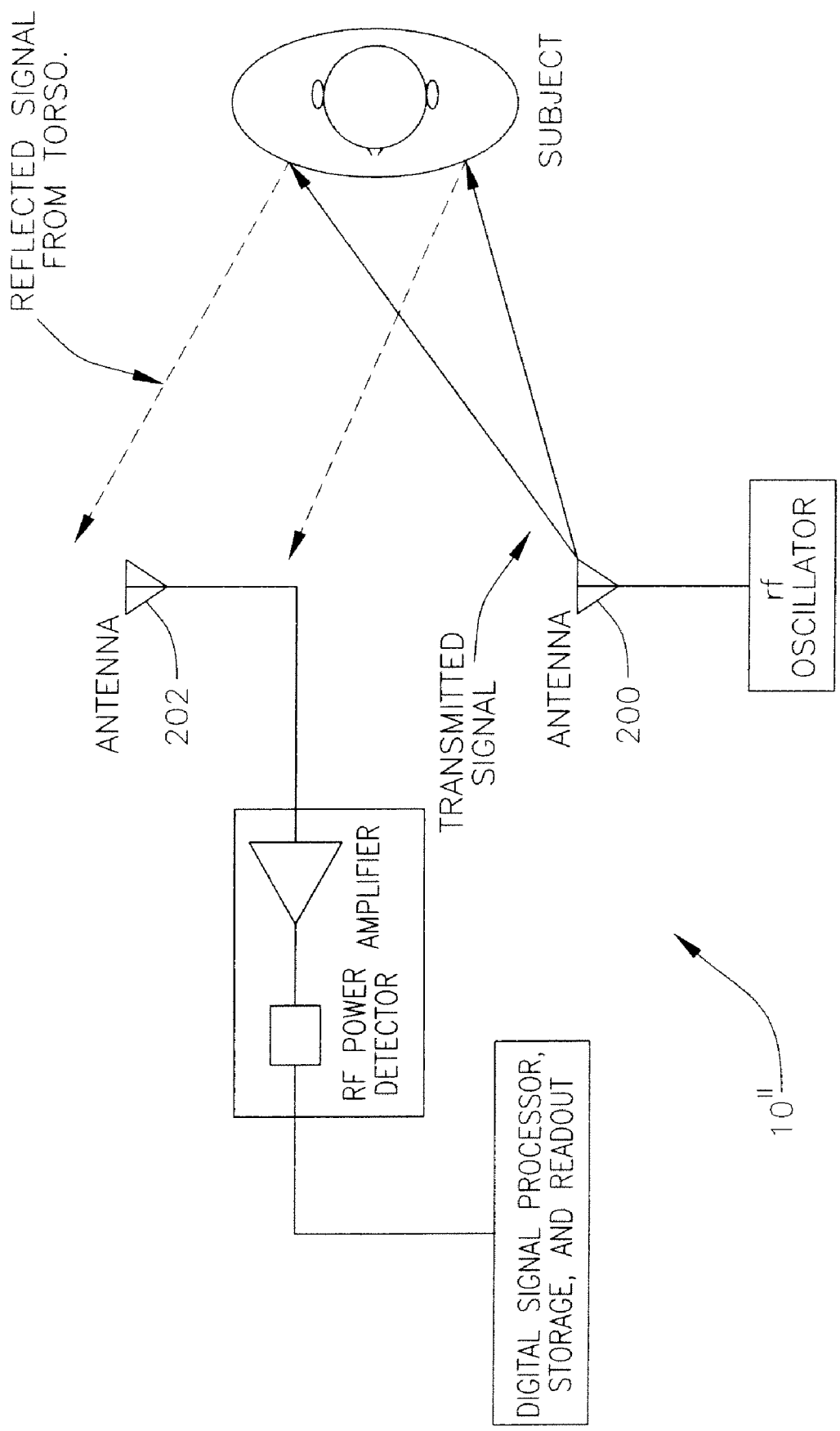
FIG. 4 is a schematic diagram illustrating an embodiment of a detector in accordance with the present invention including separate antennas for generating and detecting an electromagnetic signal.

An embodiment of a remote-detection system in accordance with the present invention that includes separate antennas for illuminating a subject and for receiving reflections is illustrated in FIG. 4. The remote-detection system 10" is similar to the embodiment illustrated in FIG. 1, except that a first antenna 200 is used to generate an electromagnetic signal beam and a second antenna 202 is used to detect the reflected electromagnetic signal beam.

Figure 5:
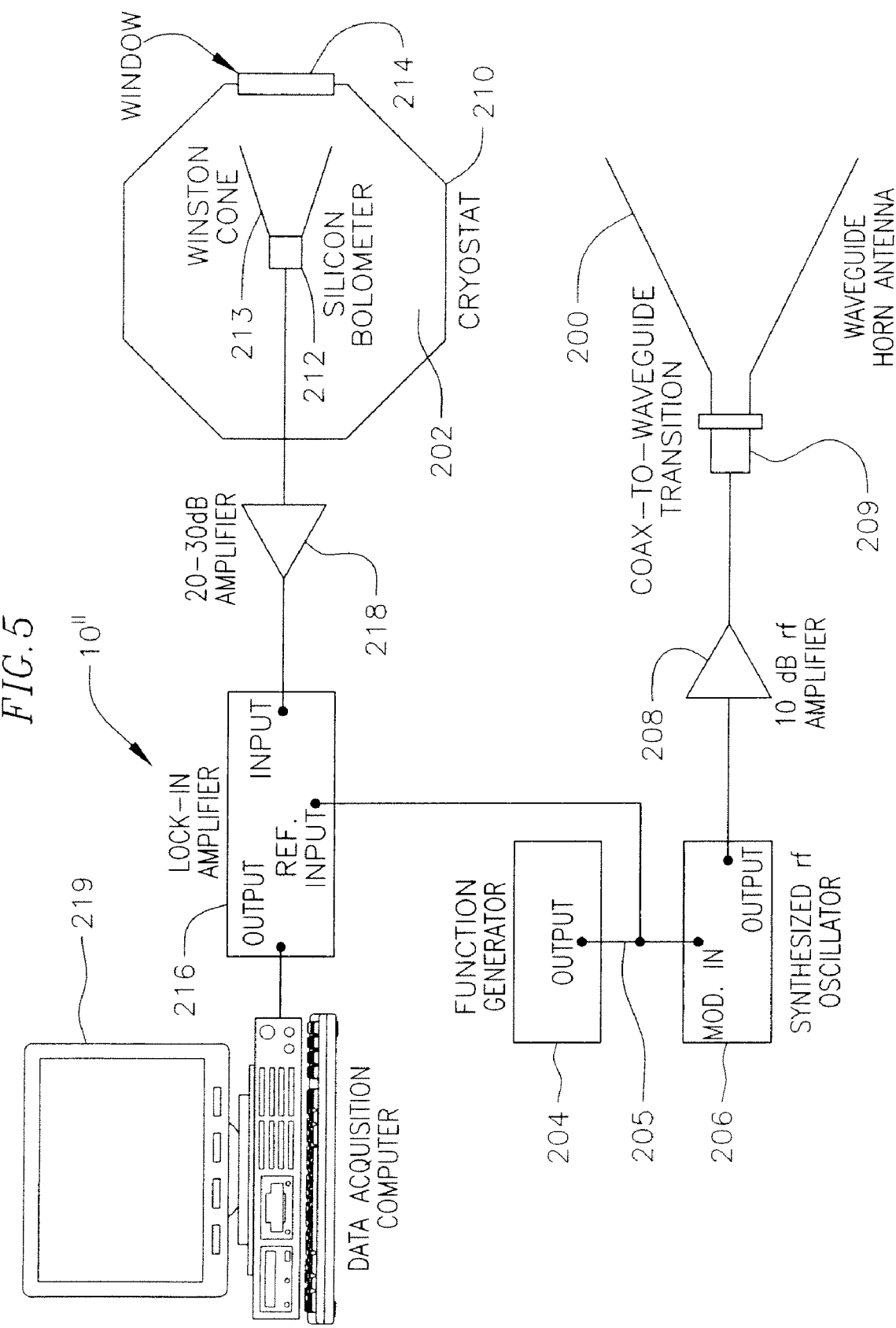
FIG. 5 is a block diagram showing an embodiment of a remote-detection system in accordance with the present invention that includes separate antennas for generating and detecting an electromagnetic signal.

A block diagram of a remote-detection system 10" including two antennas is shown in FIG. 5. The remote-detection system 10" includes a function generator 204 that is connected to a common node 205. A synthesized RF oscillator 206 is also connected to the common node 205 and to a first amplifier 208. The output of the first amplifier is provided to a waveguide horn antenna 200 via a coax-to waveguide transition 209. A second antenna 202 is contained in a cryostat 210 and includes a silicon bolometer 212 and a Winston cone 213. The electromagnetic signal is admitted through a window 214 in the cryostat and outputs from the silicon bolometer are provided to a lock-in amplifier 216 via a second amplifier 218. The lock-in amplifier is connected to the function generator 204 via the common node 205 and to a data acquisition computer 219.

The synthesized RF oscillator 206 produces an electromagnetic signal in the range of 20 GHz and can be implemented using a Model 83723B manufactured by Hewlett-Packard. The amplitude of the signal is modulated by a one kilohertz range signal generated by function generator 204 which is implemented using a Model 33120A manufactured by Hewlett-Packard. The signal is amplified by first amplifier 208 which can be implemented using a 10 dB RF amplifier such as a Model 8349B manufactured by Hewlett-Packard.

The waveguide horn antenna 200 produces the radiated signal beam and can be implemented using a Model 33120A manufactured by Microlab/FXR of Livingston, N.J. The cryostat 210 with silicon bolometer 212 detects the amplitude of the reflected electromagnetic signal and can be implemented using a Model HDL-5 manufactured by Infrared Laboratories, Inc. of Tucson, Ariz. ("Infrared Laboratories"). The second amplifier 218 boosts the output of the silicon bolometer 212 and can be implemented using a 20-30 dB amplifier such as a Model LN-6C manufactured by Infrared Laboratories. The lock-in amplifier 216 detects the signal output from the second amplifier 218 synchronously with the one kilohertz range modulation signal generated by function generator 204, and can be implemented using a Model SR830 manufactured by Stanford Research Systems. The data acquisition computer 219 is implemented using an Apple Macintosh 8600/300.

In addition to detecting physiological activity comprising the pumping of the heart, respiration, and/or a change in blood volumes or other internal bodily volumes, a remote-detection system in accordance with the present invention is capable of observing the changes in electromagnetic signal reflected by the subject due to ionic signals flowing within the body, such as those associated with nerve impulses. This is demonstrated by the ability of a remote-detection system in accordance with the present invention to detect changes in electromagnetic signal reflected by the subject due to electrical stimulation applied to the subject.

Figure 6:
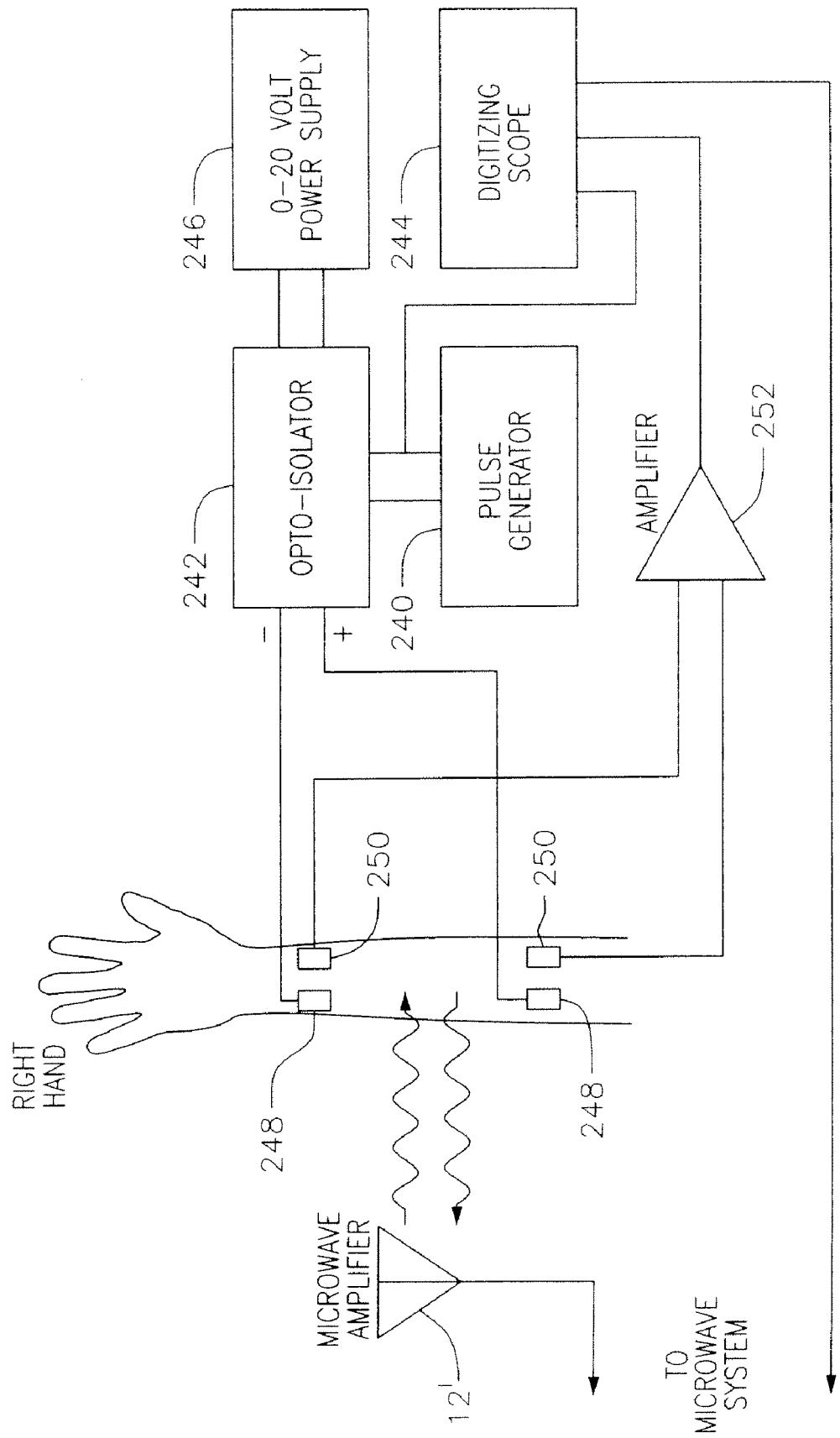
FIG. 6 is a block diagram of a test system for applying an external electrical stimulation to the body of a subject and comparing the results from a system in contact with the subject and from a remote-detection system in accordance with the present invention.

Another remote detection system in accordance with the present invention is illustrated in FIG. 6. The system is configured to measure electro-stimulation of nerves in a subject's arm. The system for generating electro-stimulation includes a pulse generator 240. The output of pulse generator 240 is connected to opto-isolator 242 and digitizing scope/spectrum analyzer 244. Opto-isolator 242 is connected to the output of 0-20 volt power supply 246 and to transmission electrodes 248 in contact with the subject's body. Reception electrodes 250 in contact with the subject's body are connected to the input of differential amplifier 252, and the output of differential amplifier 252 is connected to the digitizing scope/spectrum analyzer 244. In addition, the antenna 12' of a detection system (not shown) in accordance with the present invention is brought into proximity of the subject's body. In the illustrated configuration, the output of the detection system can be compared with measurements of the electro-stimulation obtained using the reception electrodes.

Pulse generator 240 generates low frequency pulses (typically less than twenty hertz) that set the frequency of pulses to be delivered to the subject. These pulses are fed into Opto-isolator 242. Opto-isolator 242 provides an isolated current to flow through the subject's body and gates for transmission into the subject's body pulses of electric current featuring a voltage of up to twenty volts provided by power supply 246. Transmission electrodes 248 conduct the pulses of electric current into the subject's body. Reception electrodes 250 develop a voltage potential between them corresponding to currents flowing through the subject's body. Differential amplifier 252 detects and amplifies the potential developed between the reception electrodes into a signal convenient for processing. A detection system in accordance with the present invention is also brought into proximity of the subject to monitor the signals reflected by the illuminated subject in the presence of the pulses applied to the subject's body. Digitizing scope/spectrum analyzer 244 monitors the output of the pulse generator 240, which serves as a reference, the output of the differential amplifier 252, which presents signals obtained using the reception electrodes, and the output of a detection system in accordance with the present invention, which presents signals detected by a monitoring system not in contact with the subject's body.

Figure 7:
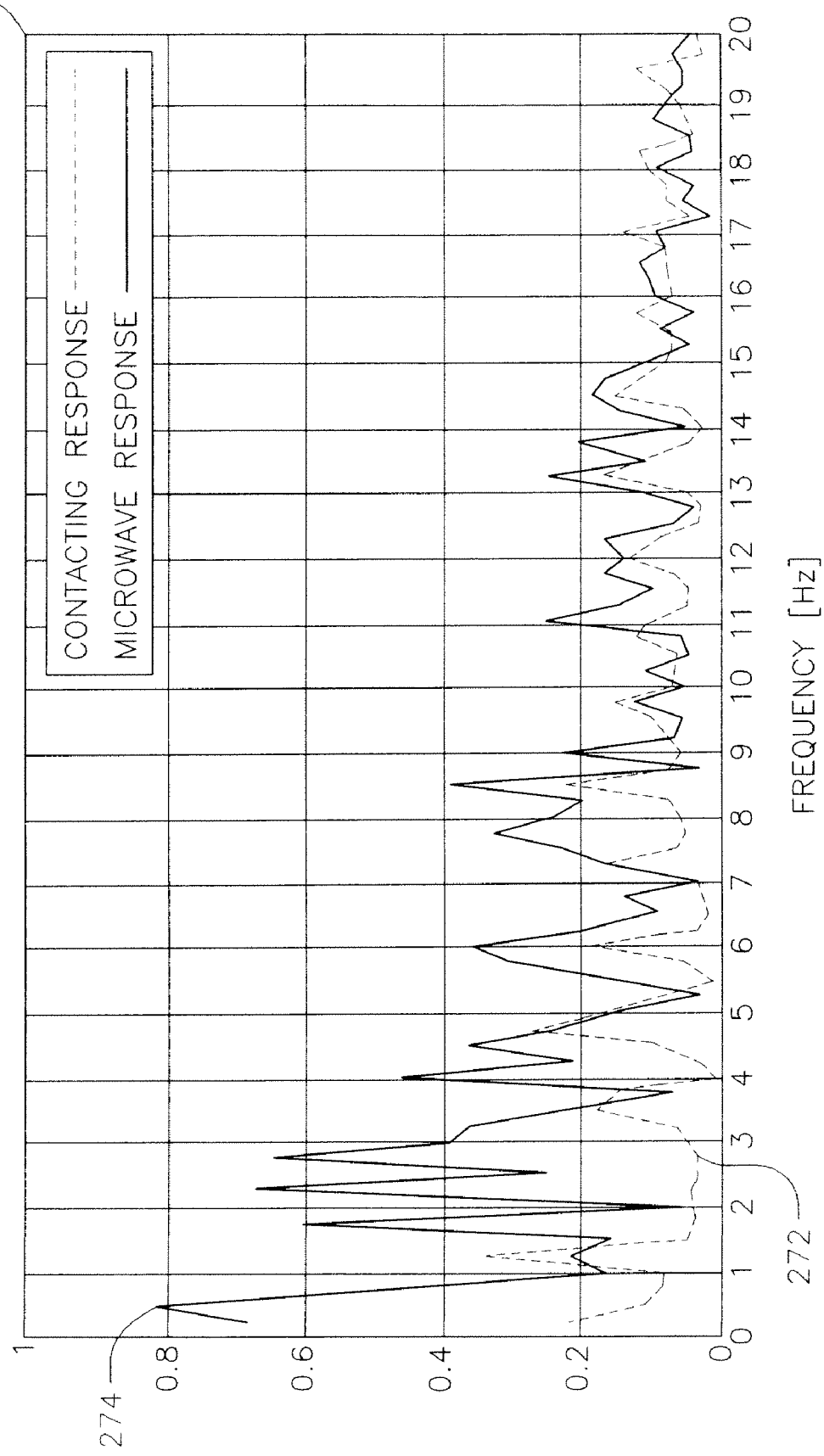
FIG. 7 is a frequency-domain graph showing the response measured by a system in contact with the subject and the response measured by a remote-detection system in accordance with the present invention when no external stimulation signal is applied to the subject.

Frequency-domain charts showing the frequencies contained in the signal obtained using the reception electrodes, and the frequencies contained in the output signal of a detection system in accordance with the present invention are illustrated in FIG. 7, FIG. 8, FIG. 9A, and FIG. 9B. The graph 270 in FIG. 7 shows the frequency-domain signal 272 obtained using the reception electrodes and the frequency-domain signal 274 output by an embodiment of a remote-detection system according to the present invention, taken during a period when no external electrical stimulation is applied to the subject's body. The graph 290 in FIG. 8 shows the frequency-domain signal 292 obtained using the reception electrodes and the frequency-domain signal 294 output by an embodiment of a remote-detection system according to the present invention, taken during a period when an external electrical stimulation consisting of pulses at a frequency of 3.5 Hertz is applied to the subject's body. Peaks in the signal 292 obtained using the reception electrodes can be seen at the fundamental frequency and several harmonic frequencies of the stimulation signal. Peaks can also be seen in the signal 294 output by an embodiment of a remote-detection system according to the present invention at the fundamental frequency and several harmonic frequencies of the stimulation signal. The graph 310 in FIG. 9A shows the frequency-domain signal 312 obtained using the reception electrodes and the frequency-domain signal 314 output by an embodiment of a remote-detection system according to the present invention, taken during a period when an external electrical stimulation consisting of pulses at a frequency of 10.5 Hertz is applied to the subject's body. A peak can be seen in the signal 312 obtained using the reception electrodes at the fundamental frequency of the stimulation signal. A peak can also be seen in the signal 314 output by an embodiment of a remote-detection system according to the present invention at the fundamental frequency of the stimulation signal. The graph 330 in FIG. 9B shows the frequency-domain signal 332 obtained using the reception electrodes and the frequency-domain signal 334 output by an embodiment of a remote-detection system according to the present invention, taken during a period when an external electrical stimulation consisting of pulses at a frequency of 15 Hertz is applied to the subject's body. Once again, a peak can be seen in the signal 332 obtained using the reception electrodes and also in the signal 334 output by an embodiment of a remote-detection system according to the present invention at the fundamental frequency of the stimulation signal.

In addition to monitoring electrical currents originating within the body, such as nerve impulses, a remote-detection system in accordance with the present invention is capable of observing electrical currents flowing through the body as a result of externally applied stimulation signals. Electrical currents flowing within the body but generated by external stimuli such as heart defibrillators, electro-shock therapy, or devices such as cardiac pacemakers that are implanted within the body but applying to the body electrical currents generated from artificial power sources, can all be monitored using a remote-detection system in accordance with the present invention as a means to detect or monitor the operation of and/or the subject's body's response to such external stimulus signals.

All the above discussion applies equally to use of an embodiment of a remote-detection system according to the present invention to monitor physiological activity of or electrical signals externally applied to a fetus within a subject's body. Because the electromagnetic signal beam is being reflected from the mother's body, monitoring of fetal physiological activity may benefit from removing or de-emphasizing from the reflected signal those elements of the signal indicative of the mother's physiological activity.

As discussed above, a remote-detection system in accordance with the present invention is capable of obtaining a considerable amount of information concerning a subject. The particular information obtained by the remote-detection system is dependent upon the application. In one embodiment, the detector monitors a subject's respiration and pulse rates. In other embodiments, the detector can obtain electrocardiographic-related waveforms and impedance cardiographic-related waveforms, or monitor muscular or neural function. Alternatively, a detector in accordance with the present invention may simply detect the presence of a living creature either as a security device or to assist rescuers in locating trapped or unconscious people.

In many embodiments involving a human subject, the signal generated by the remote-detection system is in a frequency range of 10 GHz to 80 GHz with a beam width of three feet at a distance of 26 feet. Typically, a three foot wide beam is sufficient to localize a single person without interference. In other embodiments, signals in the range of 1 GHz to 100 GHz can be used. Alternatively, embodiments could use signals in the range of 100 MHz to 200 GHz.

The width of the beam required depends on the application. For example, a broad beam could be used where a detector is attempting to detect the presence of a life form in a collapsed building. A narrow beam could then be used to determine the specific location of the detected life form. In medical diagnostic applications, an appropriate beam would have sufficient width to obtain reflections from the required portions of the subject's body and be sufficiently narrow to avoid unwanted reflections. Where Microwave Monolithic Integrated Circuit ("MMIC") technology is used to construct remote-detection systems in accordance with the present invention, a patch antenna array at 18 GHz which is approximately 4 inches on a side could produce the three foot wide beam described above at a distance of 20 feet. The effective range of the system would effectively scale with antenna size and transmitted power. Where antenna size is an issue, increasing the frequency of the electromagnetic radiation would enable the construction of smaller antennas, though the penetration through barrier would decrease.

FIG. 10 is a schematic view of a remote-detection system in accordance with another embodiment of the present invention illuminating a subject with an electromagnetic signal. For clarity only, motion and dielectric information carrying components of the reflected signal are shown spatially separated. In accordance with another exemplary embodiment of the present invention, a new 18 GHz active measurement technique is described which can remotely measure a person's impedance-cardiographic-related, phonocardiographic-related, and electrographic-related waveforms simultaneously. Using less than 1 milliwatt of RF power, the waveforms have been measured up to distances of 5 meters. Such measurements have also been obtained through (non-metallic) barriers such as walls. Since the method depends on the time-dependent permittivity and mechanical properties of the tissue, such waveforms can be obtained from most any area of the body. Results will be shown for measurements of the chest, lower abdomen, head, and leg. Larger signal amplitude variations driven by the physical motion of the chest/torso during breathing provide a means to remotely measure respiration rate at the same time. The RF system uses conventional off-the-shelf components, and a handheld unit could readily be made with existing manufacturing methods. The potential medical, search & rescue, and other commercial applications, of this capability, as well as its limitations, will be discussed.

As depicted in FIG. 10, an RF oscillator 400 generates a microwave signal that is coupled to a high-directivity antenna 401 by a circulator 402. The antenna 401 forms a narrow beam which is directed at the patient 403. A small fraction of the signal reflected back from the patient is picked up by the same antenna 401. The received signal is then amplified by amplifier 404 and the power level measured with a simple RF direct detector 405. A laptop computer 406 analyzes the time-dependent waveform and provides the readout and/or storage of the data.

The magnitude of the reflected signal for normal incidence is given by:

$$\frac{Pr(t)}{P_i} = \left|\frac{\sqrt{\varepsilon(t)} - 1}{\sqrt{\varepsilon(t)} + 1}\right|^2, \quad \text{Eqn (1)}$$

where $P_i$ is the power of the incident signal, and $P_r(t)$ is the reflected power level. $\varepsilon(t)=\varepsilon 0+\Delta\varepsilon(t)$ is the time-dependent complex dielectric value, or permittivity, of the illuminated tissue, where $\varepsilon 0$ is the large static part and $\Delta\varepsilon(t)$ is the small time-dependent part, as previously discussed. The permittivity of air is taken to be 1. There are two contributions to the time-dependent permittivity: (1) the volume of blood present in the tissue, and (2) the concentration of ions ($Na^+$, $Cl^-$ and others) in the extracellular fluid, water. The average concentration of the various ions in the extracellular fluid have been well measured (see M. J. Peters, J. G. Stinstra, and I. Leveles, "The electrical conductivity of living tissue: a parameter in the bioelectrical inverse problem" Modeling and Imaging of Bioelectrical Activity, Principles and Applications, pp. 281-319, Bin He (editor), Plenum Publishers (2004), which is herein incorporated by reference), and is dominated by Cl— and Na+. These values can be used to calculate the permittivity of this fluid, that is accurate at GHz frequencies and over a range of concentrations and temperatures, as discussed in W. Ellison, A. Balana, G. Delbos, K. Lamkaouchi, L. Eymard, C. Guillou, and C. Prigent, "New permittivity measurements of seawater", Radio Science, Vol. 33, Number 3, pp. 639-648, May-June (1998), which is herein incorporated by reference, and C. Guillou, W. Ellison, L. Eymard, K. Lamkaouchi, C. Prigent, G. Delbos, G. Balana, S. A. Boukabara, "Impact of new permittivity measurements of sea surface emissivity modeling in microwaves", Radio Science, Vol. 33, Number 3, pp. 649-667, May-June (1998), which is herein incorporated by reference. Small changes in ionic concentration driven by the electrical activity of the heart, can be estimated from the cardiac surface potentials using standard electrochemical theory. Thus $Pr(t)/P_i$ can be related back to the cardiac-driven surface potentials, and thus provide cardiac-related waveforms. And as previously discussed, the waveform of $Pr(t)/P_i$ also contains contributions from the volume of blood present in the tissue. As discussed below, the reflected microwave waveform also contains a time-dependent part due the extremely small motions (i.e., vibrations) of the torso caused by the heart sounds which constitute the phonocardiogram,(PCG). All of these contributions are periodic in time, and are driven by the mechanical and electrical action of the heart.

One additional source of modulation of the reflected microwave beam is the motion of the chest caused by respiration. The motion of the chest does not change the amplitude of the reflected beam at the air/skin interface, but it does change the angle of the RF power scattered back in the direction of the antenna. Thus, the amount of signal that is directed back into the narrow beam pattern of the antenna varies with the respiration. This signal variation is quite large and is easily measured.

Equation (1) can equally as well be written in terms of complex impedances:

$$\frac{Pr(t)}{P_i} = \left|\frac{Z_1 - Z_2(t)}{Z_1 + Z_2(t)}\right|^2 \quad \text{Eqn (2)}$$

where $Z_1$ is the impedance of free space ($\approx 377$ ohms), and $Z_2(t)$ is the time-dependent impedance of the tissue illuminated by the incident beam. This form is convenient for correlating the reflected microwave power with the measurements of the impedance-cardiographic waveform. The volume of blood in the upper torso is considered to be one of the dominant contributions to the time-dependent impedance of the torso. This thoracic impedance waveform consists of the basal impedance and a small time-dependent impedance: $Z(t)=Z_0+\Delta Z(t)$. The component $\Delta Z(t)$ constitutes the Impedance Cardiogram (ICG), which along with its time derivative dZ/dt, can yield information about the mechanical properties of the heart, such as the timing of valve actions, the stroke volume, and total output of the heart. The magnitude of the basal resistance is usually several tens of ohms (30-60 ohm, for example), whereas $\Delta Z(t)$ is typically about 0.1 ohm, or less. However, this small resistance change readily modulates the amplitude of the reflected microwave signal. As will be seen from the measurement data, when properly analyzed, this signal component closely follows the ICG ($\Delta Z(t)$) waveform as measured with conventional contacting electrodes; and the derivative of the microwave signal strongly correlates with dZ/dt; even though the microwave signal only samples the blood content of the skin, and not the entire volume of the torso.

The entire waveform of the reflected microwave signal that contains the ECG-related, ICG-related, and PCG-related information will be referred to as the "microwave cardiogram." This distinguishes it from the respiration component of the signal. It is also a convenient terminology when discussing comparisons with the ECG, ICG, and PCG.

Figure 11:
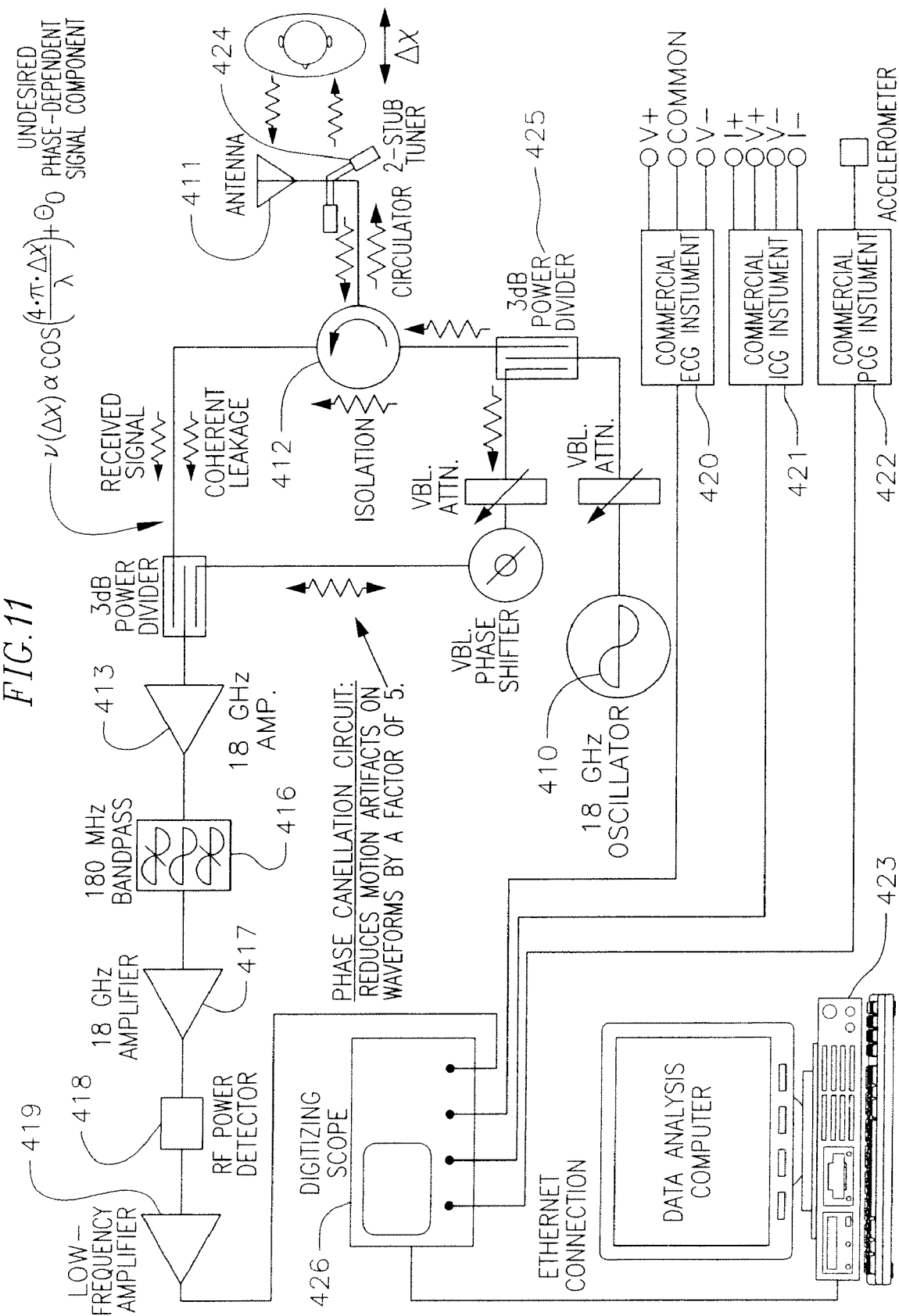
FIG. 11 is a block diagram of a test system showing an arrangement of microwave components for transmission and reception of the microwave signal, a phase-cancellation circuit section, and commercial ECG, ICG, and PCG instruments according to an exemplary embodiment of the present invention.

FIG. 11 is a block diagram of a test system showing an arrangement of microwave components, and commercial ECG 420, ICG 421, and PCG 422 instruments according to an exemplary embodiment of the present invention. All the RF components are coaxial-based, except for the circulator 412, 2-stub tuner 424, and antenna 411 which are waveguide components. An RF oscillator 410 is used to generate an 18 GHz signal. For most experiments, the power level was less than or equal to a milliwatt. This signal is coupled to the waveguide horn antenna 411 by a 3-port circulator 412. The isolation of the circulator 412 (typically about 25 dB) is an important parameter, as it determines how much of the source signal leaks into the receiver path. This leakage makes the receiver sensitive to the gross motions of the subject. To minimize this undesired effect, a phase cancellation circuit is included which takes a piece of the source signal, by way of a power divider 425, and allows for adjustment of its phase and amplitude so that by inserting it into the receiver path, it can be adjusted to cancel most of the leakage signal. This reduces gross motion artifacts by about a factor of five. However, very small amplitude motions, such as vibrations of the surface of the torso caused by the heart sounds, can still be measured. In this way, the system is capable of measuring a waveform that is directly related to the phonocardiogram of the subject, without the need for the phase-stabilized homodyne techniques employed by radar methods. A 2-stub tuner 424 is used to minimize the impedance mismatch of the horn antenna 411, and thus reduce standing-wave effects. The reflected signal is picked up by the antenna 411 and coupled through the circulator 412 to a low-noise 18 GHz amplifier 413 followed by a narrow bandpass filter 416, which reduces the overall noise of the system. The signal is then further amplified by a second 18 GHz amplifier 417 and fed to an RF direct detector 418, which produces a voltage linearly proportional to the total signal power. An instrumentation amplifier 419 with a variable gain, set to between 15 dB to 20 dB, boosts the signal from the detector. The signal is then collected by a Tektronix TDS 5104 digitizing oscilloscope 426 at a sampling rate of at least 1250 samples/second. This is a 4-channel scope which simultaneously measures the microwave signal, ECG, ICG, and PCG waveforms, thus making all 4 waveforms synchronous in time. A personal computer 423 was used for data analysis.

Figure 12:
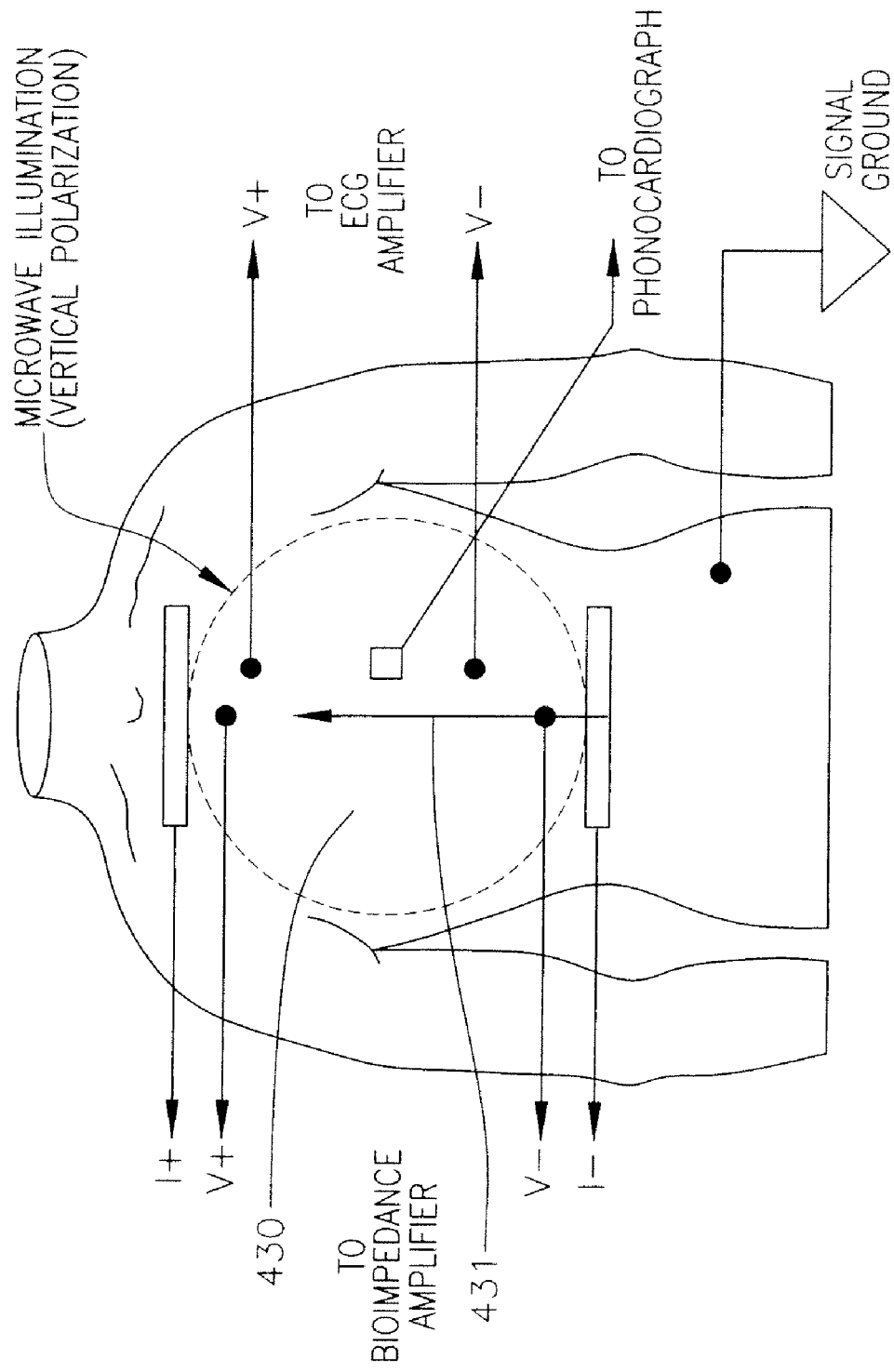
FIG. 12 is a diagram showing a placement of electrodes for the ECG and thoracic-impedance/ICG measurements, and the location of the accelerometer (black square) for the PCG measurements, with the shaded circle indicating an area of the torso illuminated by the microwave beam and the vertical arrow showing the polarization of the microwave beam.

A conventional contacting single-lead ECG, the ICG, and PCG were measured simultaneously with the microwave cardiogram. FIG. 12 is a diagram showing a placement of electrodes for the ECG and ICG measurements, the accelerometer for the PCG measurement, with the shaded circle 430 indicating an area of the torso illuminated by the microwave beam and the vertical arrow 431 showing the polarization of the microwave beam. The ECG is measured using conventional, self-adhesive, Ag/AgCl electrodes. Two different amplifiers have been used for the ECG measurements. One is a commercial cardiotachometer with an input impedance of $\geqq 100$ mega-ohms and a bandwidth of 1 Hz-58 Hz. The other is a general purpose bioamplifier with an input impedance of $\geqq 10,000$ mega-ohms and selectable bandwidths of 100 Hz up to 50 kHz.

The thoracic impedance cardiogram was measured using a commercially available system. All measurements were made with a 50 KHz, 100 µA current source applied to the torso using 25 cm long strip electrodes. The corresponding voltage drop was measured using metal-disk electrodes. It was found that these electrodes gave a better correlation with the microwave signal than the strip electrodes, which are more commonly used for ICG measurements. This is related to the fact that the intensity profile of the microwave beam is Gaussian, and hence decreases with increasing radius from the center of the beam. Strip-shaped voltage electrodes would be better suited to a uniform illumination intensity with no radial-dependence.

The phonocardiogram was measured with a commercially available, silicon-based analog accelerometer module. This module measured about 1-inch on a side, and weighed 10 grams. It was powered by a 12 volt DC power supply, and has a sensitivity of about 2000 mV/G, where G is the acceleration due to gravity, 9.8 m/s$^2$.

For most measurements, the transmitted power level was between 50 µW and 1 mW. The typical distances between the subject and the horn antenna were in the range of 0.3 m to 1.0 m, which is in the far-field of the horn (longer distance measurements were also made, up to 5 m, as discussed later). Using the calculated single-mode Gaussian beam pattern of the horn, this resulted in a power density of $\leqq 0.1$ mW/cm$^2$, incident on the subject's chest. The issue of safe RF power exposure levels has been extensively studied experimentally and theoretically over the past several years, primarily due to concerns related to the increased use of modern telecommunications and computer equipment by the general public. The general consensus is that RF exposure is safe at low power levels. The currently accepted Maximum Permissible Exposure (MPE) for spot illumination in the range of 18 GHz is about 25 mW/cm$^2$, as set by the IEEE Standards Coordinating Committee 28. The power levels used for the measurements reported here are at least 200 to 1000-times lower than the MPE, and hence are considered very safe.

The ability of a remote-detection system in accordance with the present invention to operate through structures or debris is dependent upon the materials composing the structures or debris. Many materials such as bricks, wood or cinderblocks are transparent to electromagnetic signals of frequencies in the ranges described above. However, water in concrete and the presence of metal can interfere with the signals received by the remote-detection system.

In other embodiments, remote-detection systems in accordance with the present invention can be used to monitor neural or muscular function. In addition, a remote-detection system could also be used as a monitor for sudden infant death syndrome or for sleep apnea. The applications of the remote-detection system also include exercise equipment, where the remote-detection system can be used to monitor pulse and/or respiration during an aerobic workout. In all instances the remote-detection system is placed a distance from the subject and measurements are made without the need for contact between the system and the subject. The applications of the remote-detection system are not limited to human subjects or human tissue. The devices and principles described above can be equally applied to detection and monitoring of other mammalian life forms.

As discussed above, remote-detection systems in accordance with the present invention can work effectively at varying distances from the subject, including considerable distances. It may be advantageous to use different distances between the subject and the remote-detection system. In a disaster scene where a remote-detection system is used to locate trapped subjects, it may not be possible to locate the remote-detection system close to the subjects to be detected. The distance between the subject and the remote-detection system may also be varied to obtain a different strength and/or width of reflected electromagnetic beam or to focus on a more specific portion of the body to the exclusion of signals returned from other portions.

Figure 13:
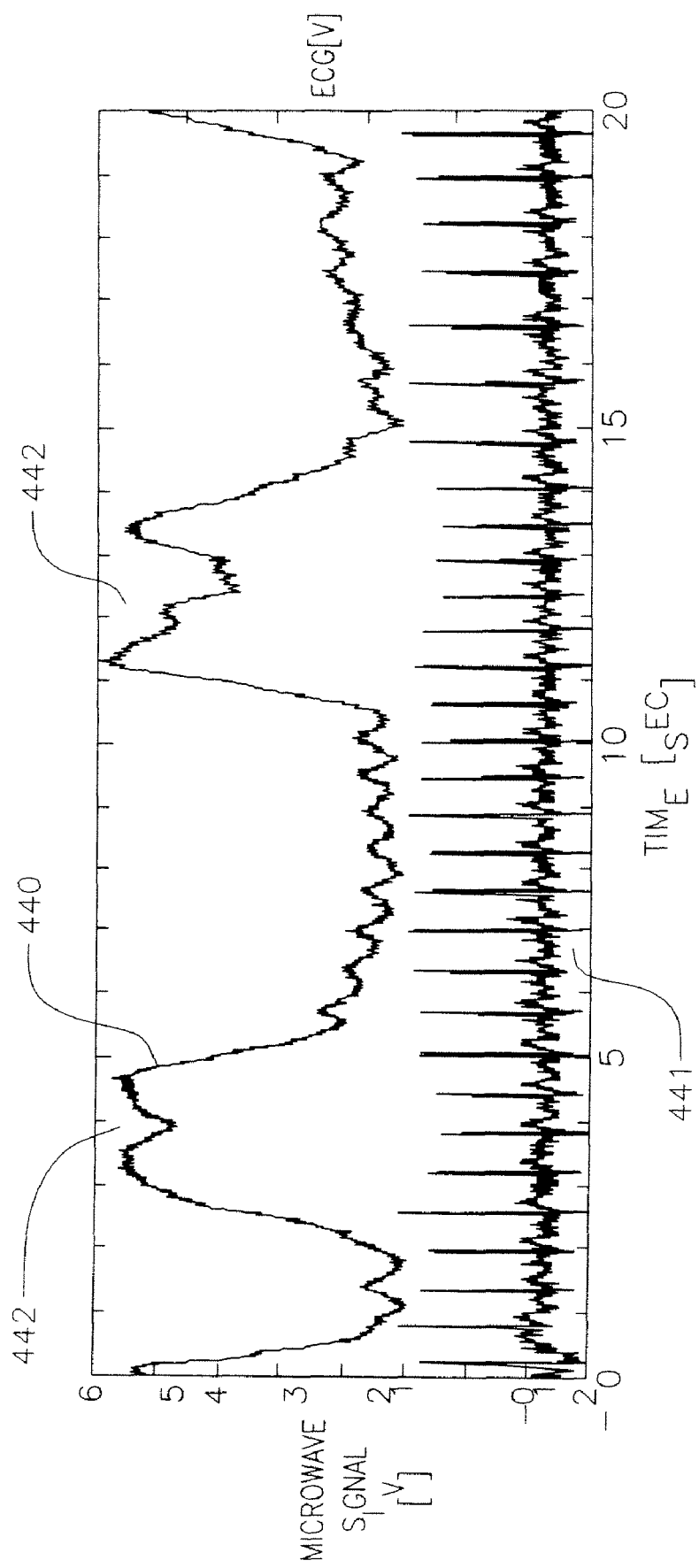
FIG. 13 is a graph showing a reflected microwave signal and a simultaneously measured electrocardiogram (ECG) from an adult male breathing normally.

FIG. 13 is a graph showing a reflected microwave signal 440 and a simultaneously measured electrocardiogram (ECG) 441 from an adult male breathing normally. The reflected microwave signal is from the torso of an adult male subject (the subject did not remove his shirt as the microwaves readily penetrate clothing). An ECG 441 was measured simultaneously for comparison. The microwave signal 440 has a large average DC offset due to the reflection caused by the mismatch of the average permittivity of the tissue with free space. The large "bumps" 442 separated by about 5 seconds are due to breaths taken by the subject. Generally these respiration signal structures are very large and easy to detect and measure. Also visible in the figure are much smaller peaks between, and on top of, the respiration signal. These peaks align precisely with the ECG signal and are a result of cardiac activity, as a closer examination of the data will show. The amplitude of these features is typically 20 to 100 times smaller than the respiration signal, and the magnitude of the static reflection level. Thus, in order to remove the comparatively large baseline shifts and allow for sensitive measurements, the detected signal was ac-coupled to the digitizing oscilloscope. The ac-coupling circuit however changes the shape of the actual microwave cardiogram signal present at the input terminal of the oscilloscope, due to the high-pass filter used to remove DC. It is thus necessary to transform the recorded signal using the transfer function of the input circuit of the oscilloscope to obtain the actual shape of the waveform at the input terminal. The ac-coupling circuit uses an analog 1-pole highpass filter with a rolloff frequency of about 6 Hz. Using simple circuit theory, the following equation relating the input signal voltage, $V_{in}$, to the voltage actually measured, $V_{meas}$, by the scope can be written as:

$$V_{in}(t) = V_{meas}(t) + \left(\frac{1}{R_1 C_1}\right) \cdot \int V_{meas}(t) \cdot dt. \qquad \text{Eqn (3)}$$

Figure 14:
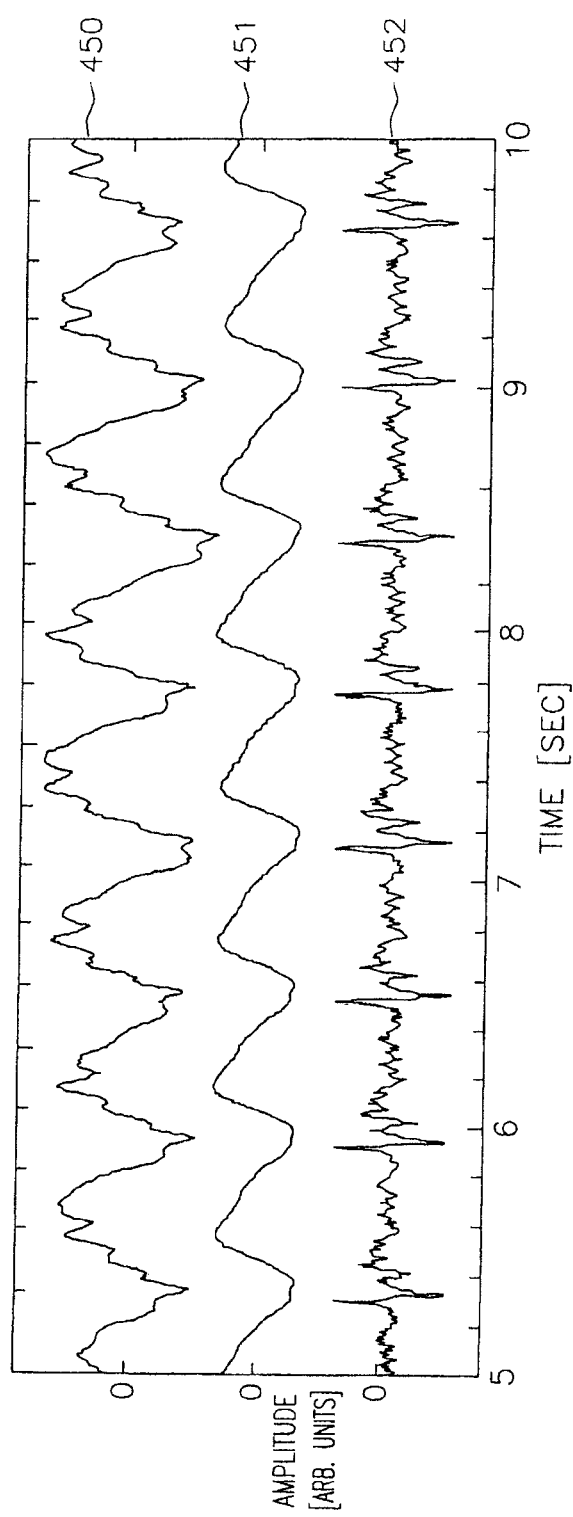
FIG. 14 is a graph showing a simultaneously measured microwave cardiogram, impedance cardiogram, and electrocardiogram with an adjusted vertical scale to allow the three curves to be shown together.

FIG. 14 is a graph showing a simultaneously measured microwave cardiogram 450, impedance cardiogram 451, and electrocardiogram 452 with an adjusted vertical scale to allow the three curves to be shown together. The value of the time constant, $R_1 C_1$, was determined from the measured step-response of the scope, and found to be approximately 25 ms. Transforming the microwave signal using Eqn (3), FIG. 14 shows the simultaneously measured microwave cardiogram 450, ICG 451, and ECG 452 of an adult male subject. As can be seen, the microwave cardiogram 450 has a large low-frequency structure (with a frequency of about 1.5 Hz), as well as periodic higher frequency structures. As apparent from this figure, the low frequency components of the microwave signal 450 are synchronous with the ICG 451. High frequency components, which are not as easily visible without the use of digital filters, are correlated with the ECG. Several data sets of this type were collected from three adult male subjects, and all showed the same correlations. Typically 20 to 40 seconds of data were collected. For measurements related to investigating the cardiac nature of the signal, the subject held his breath to avoid the large amplitude variations related to respiration.

FIG. 15 is a graph showing an ICG waveform 460 (solid curve) that shows a characteristic steep rise due to the ventricular systole and shows a lowpass-filtered microwave cardiogram 461 (dashed curve) with adjusted amplitude to match the ICG waveform 460. The graph shows that the agreement is quite good given the simple signal processing used, and demonstrates that an analog of the basic ICG waveform 460 is contained in the microwave cardiogram 461. As depicted in FIG. 15, the filtered microwave cardiogram signal 461 is superimposed on the simultaneously measured ICG waveform 460. Only the real-part of $\Delta Z(t)$ is shown as the imaginary part was nearly zero for all measurements. Further, decreasing impedance is shown in an upward direction, as is commonly done with this type of waveform. The microwave signal was digitally processed using a finite impulse response (FIR) lowpass filter with a rolloff frequency of $f_{LP}=2$ Hz to eliminate the sharp high-frequency components. The filter used 450 coefficients weighted by a Hamming windowing function. The amplitude of the signal was then adjusted to give the best average match to the ICG for comparison purposes. As can be seen in FIG. 15, the lowpass-filtered microwave signal 461 agrees well with the ICG waveform 460. The lowpass-filtered microwave signal 461 displays the typical shape of this type of bioimpedance waveform with a steep rise (decreasing impedance) during ventricular systole, followed by a slower drop (increasing impedance) with a small bump indicating the smaller impedance increase during diastole.

FIG. 16 is a graph showing an ICG 470 measured with contacting electrodes, the derivative of the ICG 471 including points indicating the A-wave (atrial systole), the C-wave (ventricular systole), the O-wave (ventricular diastole), and the points B and X (aortic valve opening and closing, respectively), and the derivative of the lowpass-filtered microwave cardiogram 472 with vertical dashed lines indicating significant similarities between the waveforms. The vertical scale for each curve was adjusted to allow the three curves to be shown together. Thus, FIG. 16 shows the ICG waveform, its derivative dZ/dt, and the derivative of the lowpass filtered microwave cardiogram. The ICG was minimally lowpass filtered to remove high frequency noise and allow for a smooth derivative. The FIR filter had a rolloff frequency of 7 Hz and 230 filter coefficients with a Hamming window. The dZ/dt waveform has been extensively studied for many years and several of its characteristic features can be related to events in the cardiac cycle. These points are labeled on the dZ/dt waveform. The A-wave corresponds to the atrial systole, the C-wave to the ventricular systole, and the O-wave to the ventricular diastole. The points B and X correspond closely to the aortic valve opening and closing, respectively. The vertical dashed lines indicate the corresponding points on the derivative of the microwave signal. There is significant similarity between these waveforms. The large C-wave is clearly present in the microwave signal. The A-wave is also present, but inverted. The O-wave appears more pronounced in the microwave signal. The B and X points are very similar between the two curves. Thus, the microwave signal could be used to remotely monitor the timing of these cardiac events.

Figure 17:
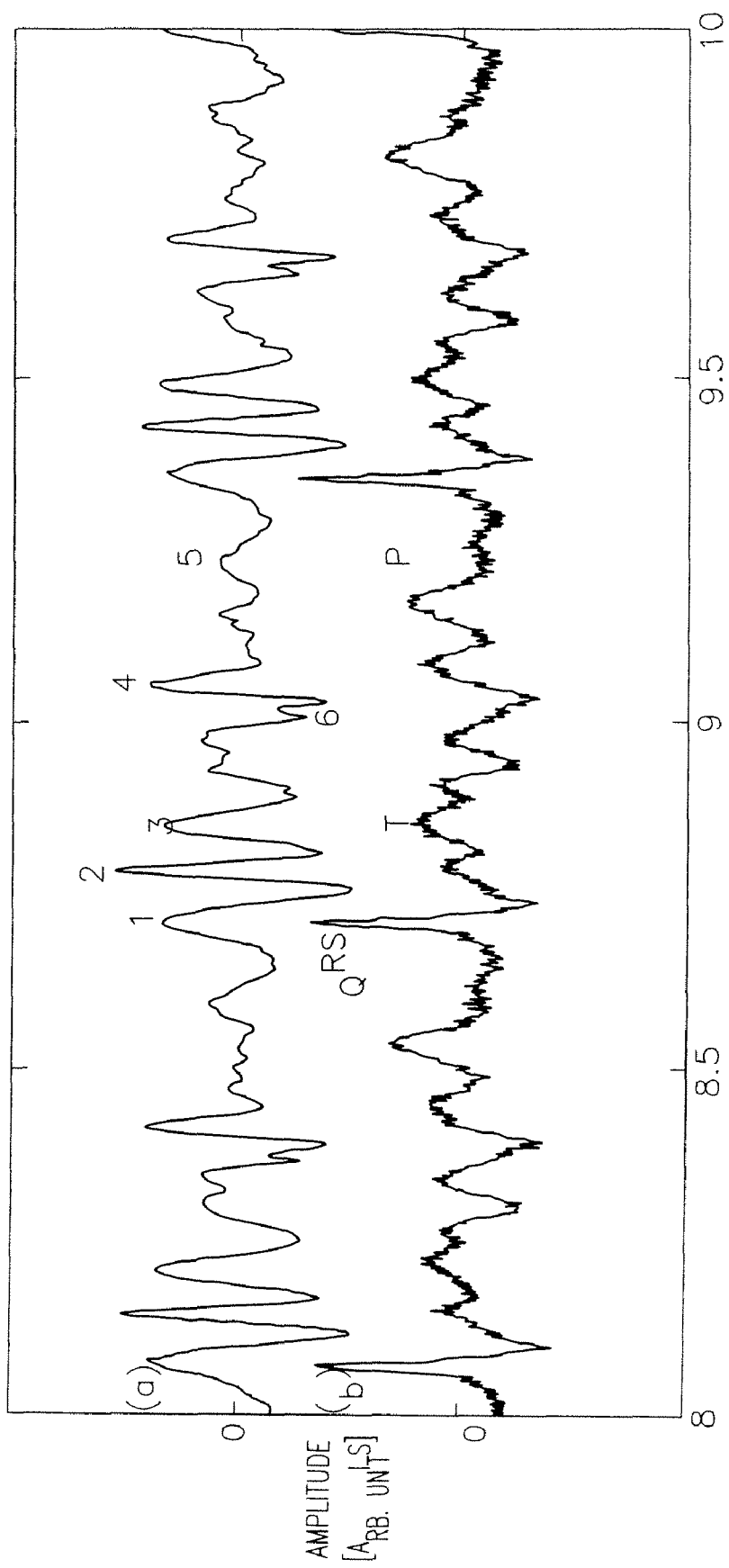
FIG. 17 is a graph showing (a) a highpass filtered microwave cardiogram, (b) an ECG measurement made with contacting electrodes placed in the region illuminated by an 18 GHz signal. Characteristic features of the ECG are labeled on curve (b). Features in curve (a) that are correlated with the ECG waveform, as well as with other cardiac-related physiology, are labeled with numbers 1 through 6.

Further analysis of the reflected microwave signal reveals that it also contains evidence of some of the characteristic features found in an electrocardiogram. As discussed earlier, an electrocardiographic signal was collected simultaneously with the microwave signal, with contacting electrodes placed on the chest, in the area illuminated by the microwave beam. FIG. 17 is a graph showing (a) a highpass filtered microwave cardiogram, (b) the wideband electrocardiographic waveform (we will refer to this waveform as an "ECG" for simplicity) measured with contacting electrodes placed in the region illuminated by an 18 GHz signal. The 2 plots, (a) and (b) show several similarities between both large and small features of the two curves. Curve (a) is the microwave signal after being digitally processed through a FIR highpass filter with a 3 dB corner frequency of $f_{HP}=12$ Hz, which removed the large amplitude, lower-frequency components related to the ICG, discussed above. In addition, very high-frequency noise was removed from the curve using nonparametric estimation based on recently developed "wavelet shrinkage" techniques. Curve (b) shows the simultaneously measured ECG signal. This waveform contains more structure than is typically present in a "diagnostic" ECG, likely due to the placement of the electrodes on the chest, near the heart, rather than on the arms. The curves were scaled so that the highest peak in each was about the same height in the plot. As can be seen, there several correlations between the two curves. The peak-like structure labeled I aligns well with the QRS-complex in the ECG. In particular, the rising curve of the slope of these two peaks agree well. However, the structure in the microwave cardiogram is broader and not as sharp as its ECG counterpart. This is due primarily to the fact that the microwave beam illuminates most of the upper torso, and thus provides more of a spatial-average of the QRS-complex. Since the QRS-complex changes shape at different points on the torso, and even reverses direction on the right side of the upper chest, it is not surprising that the microwave counterpart has a more smeared-out shape. Also, the QRS-complex is a spatially dipolar potential that will affect different parts of the beam differently. These is also a reproducible peak, 3, that aligns well with the central peak of the T-wave. Numerous other measurements of this type have typically shown a well-defined peak or hump aligned with the T-wave. The T-wave may be more easily seen since it has a single polarity on the chest, and will more uniformly reflect the microwave beam. There is also a structure in the vicinity of the P-wave, but the correlation is not as strong. This is likely because the P-wave potential is quite low and so would affect the permittivity of the tissue less that the other components of the ECG. There are also two reproducible, strong, peaks, 2 and 4, which occur just after the QRS-complex and the T-wave, respectively. These are precisely the locations one would expect to see the first and second heart sounds, respectively. In fact, as discussed later, due to the short-wavelength of our 18 GHz signal, the test system is sensitive to the very small amplitude vibrations at the surface of the chest caused by the heart sounds. Finally, it is interesting to note that there is a small reproducible peak, 6, that appears in the microwave cardiogram, but not in the contacting ECG waveform. It may represent some additional cardiac physiology that is not seen in a conventional ECG. Higher resolution measurements and clinical studies will be needed to investigate this point.

It is possible to obtain the same basic microwave cardiogram signal from a person at a distance of several meters as it is for distances less than or equal to 1 m as discussed above. A higher-gain antenna which produces a more narrowly collimated beam was used. The cross section of a typical adult will still intercept most of the microwave beam, but at a larger distance from the antenna, thus maintaining a good S/N ratio. Using a waveguide horn antenna coupled with a 25 cm diameter Teflon lens, which produced a 3 dB full beam width of 6-degrees (i.e., a gain of 28.5 dBi), measurements of microwave cardiograms were made at a distance of 5 m (17 ft) (the longest unobstructed distance available in the laboratory). Also, to improve the S/N ratio for these measurements, the data was digitized at 12.5 KS/sec and then averaged in groups of 10 data points to produce an effective sampling rate of 1.25 KS/sec. A single-lead ECG using the cardiotachometer, with contacting electrodes on the arms, was collected simultaneously; and no ICG was collected. The purpose here is to show that the technique works over larger distances, and not to make another detailed comparison with the ECG and ICG waveforms.

Figure 18:
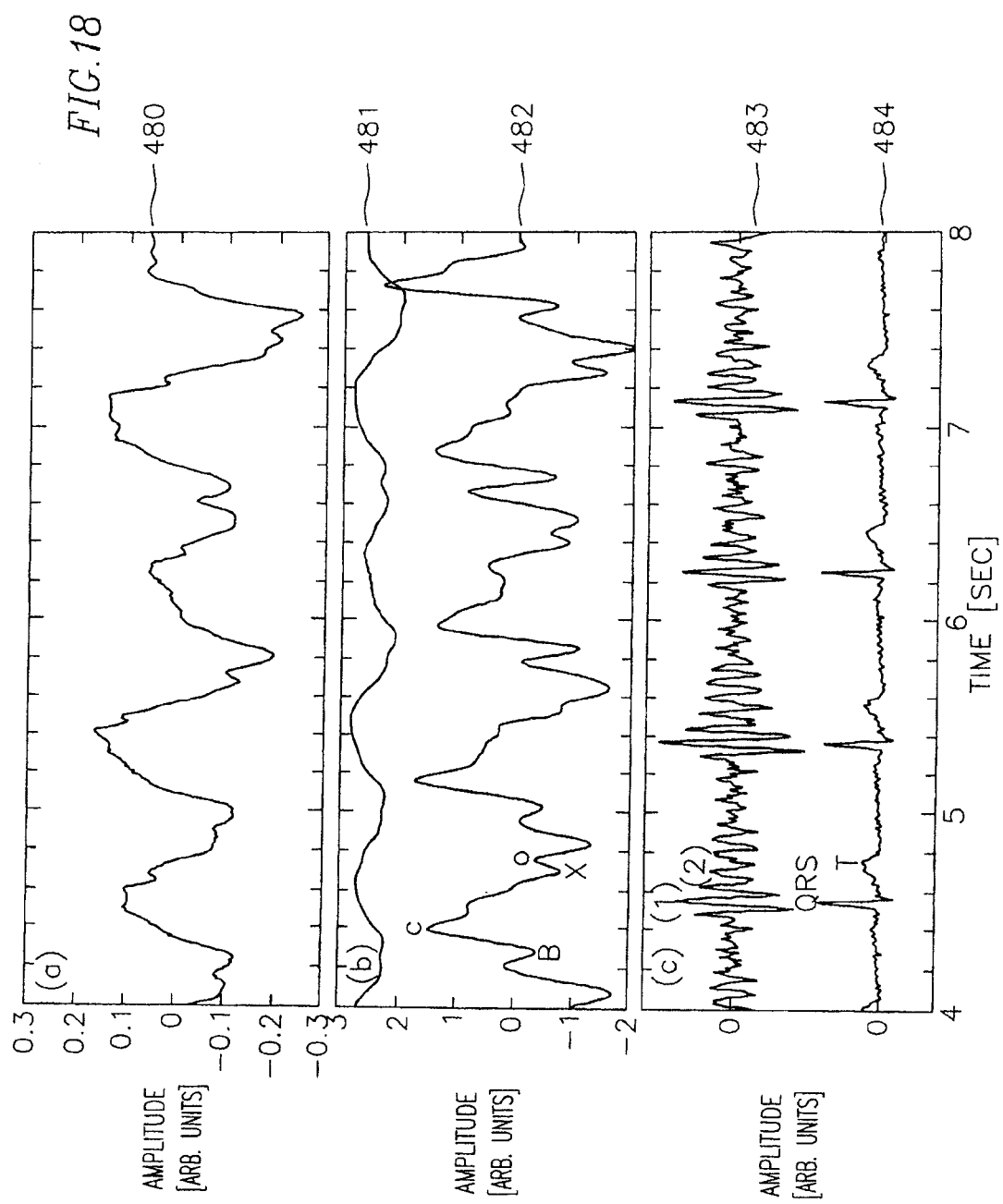
FIG. 18 is a graph showing (a) microwave cardiogram measured at a distance of 17 feet, (b) the lowpass filtered microwave cardiogram and the derivative of the lowpass filtered microwave cardiogram with characteristic points of an ICG identified, and (c) the highpass filtered microwave cardiogram and a reference ECG measurement made with contacting electrodes.

FIG. 18 is a graph showing (a) microwave cardiogram 480 measured at a distance of 17 feet, (b) the lowpass filtered microwave cardiogram 481 and the derivative of the lowpass filtered microwave cardiogram 482 with characteristic points of an ICG identified, and (c) the highpass filtered microwave cardiogram 483 and a reference ECG measurement 484 made with contacting electrodes.

The microwave cardiogram 480 was obtained from an adult male sitting 5 m from the antenna. The microwave cardiogram shows broad periodic structure with smaller, sharp features as seen in FIG. 14.

The bioimpedance-related curve 481, ΔZ, and its derivative 482, dZ/dt, is obtained from curve (a) using the digital filtering techniques discussed earlier. The large C-wave (ventricular systole) is clearly seen. The smaller diastolic O-wave, as well as other characteristic features also appear to be present. The detailed shape of dZ/dt is not expected to look exactly like that obtained from a typical contacting ICG, in this case. At a distance of 5 m, the diameter of the beam at the subject was about 77 cm. Thus, the beam illuminated more than just the chest or upper torso. Clearly the bioimpedance-related signal obtained in this case would be expected to contain some of the ICG components, as well as other features. It is well-known that an ICG waveform is strongly dependent on the type and placement of the electrodes. The area illuminated by the beam in this case would certainly correspond to some non-standard arrangement of electrodes. For applications where a detailed ICG may be needed from a distance, a properly-designed antenna with an appropriately sized beam would need to be used.

The highpass-filtered waveform 483 was obtained using the same signal processing techniques for the microwave cardiogram described earlier. There is reasonable correlation between the structures related the first heart-sound and the QRS-complex. There are also reproducible components in the microwave signal at the position of the T-wave in the ECG. The contacting ECG 484 is provided for reference.

These results demonstrate that it is possible to obtain electrocardiographic-related and bioimpedance-related waveforms at distances of at least 5 m. The maximum usable distance will ultimately be limited by tradeoffs between RF power, beam size, and the isolation of the circulator, to maximize the overall S/N ratio. For medical-related applications, where particular waveforms are required, antennas may be engineered to produce specific beam shapes, and more sophisticated signal processing algorithms may be developed.

A significant application for remote-sensing human vital signs is identifying the presence of a person behind a barrier (e.g., collapsed walls and floors, or other rubble at a disaster site). It is primarily important in this case to identify waveforms with human ECG-related and ICG-related features, in order to distinguish it from an object which might be oscillating (or repetitively moving) with frequency components between 1 Hz and 2 Hz: the typical range for a human heart beat. Three types of barriers were constructed to test the effectiveness of this microwave technique for this application. The barriers are: 1) a 4 ft wide by 8 ft tall section of a typical residential interior wall, constructed with standard 2×4s on 16 inch centers for the frame, with 0.5 inch thick sheet-rock panels on both sides; 2) a standard 36 inch wide by 80 inch tall by 1.75 inch thick wooden door; and 3) a cinder-block wall 49 inches wide by 46 inches tall by 8 inches thick, the blocks being clamped together in a wood frame using 0.5 inch diameter threaded steel rods which simulated the rebar found in actual walls of this type. The microwave cardiogram test system was used to measure the roundtrip attenuation at 18 GHz of each barrier. The lens-antenna, described above, was used to produce a narrow beam. A 25 cm diameter, 2-blade, metallic chopper-wheel running at about 10 Hz was used to produce a triangle-wave modulation of the reflected microwave beam. The chopper was placed at a distance of 4.3 m from the lens-antenna. The barriers were inserted into the beam at a distance of 3.5 m from the antenna. The first 20 seconds of data were taken without the barrier, to establish the zero-attenuation level. Then the barrier was inserted and an additional 20 seconds of reflection data were taken. Any barrier will cause some reflected power, which can produce standing-waves, resulting in baseline shifts of the measured signal level. To get an approximate measure of this effect, the barriers were wiggled slightly back and forth during the measurements, which produced some amplitude variations in the received signal. The result for the interior wall barrier was that between 61% and 92% of the transmitted signal returns to the system. The standing-wave effect can be minimized in a practical application, simply by directing the microwave beam at a slight angle to the barrier, thus avoiding a direct reflection back into the antenna. Measurements were made for the other barriers. For the door, 13% to 39% of the signal was returned, and for the cinder-block wall, 1.5% to 4% of the signal was returned. These attenuation factors are not very large and are not expected to significantly limit the usefulness of this technique, since the transmitted power can simply be increased to compensate for the loss. However, the S/N ratio will decrease due to the directivity of the circulator. More sophisticated signal processing might be necessary for a barrier like cinder blocks; or lower (and hence more penetrating) frequencies might also be desirable in some cases.

FIG. 19 is a graph showing (a) microwave cardiogram 490 measured for an adult male located behind an interior wall; (b) the lowpass filtered microwave cardiogram 491 and its derivative 492 with the A-wave, O-wave, C-wave, and the X and B points identified; and (c) the highpass filtered microwave cardiogram 493. The microwave cardiogram 490 is from a person positioned 2 feet behind the interior wall barrier. The microwave antenna was located 3 feet in front of the barrier. A wavelet transform and a FIR lowpass filter with a rolloff frequency of 40 Hz and 150 filter coefficients were used to reduce noise on the highpass filtered microwave cardiogram 493. The sharp structures (point (1)), seen many times before in this type of waveform, in close proximity to the first heart sound and the QRS-complex, is clearly seen here, as is a smaller peak (point (2)) approximately midway between the large peaks, which is usually correlated with the second heart sound. Thus, even with simple signal processing, it would be possible to identify the presence of a trapped victim behind a barrier with a high probability.

For search and rescue applications, an important practical issue is that the microwave beam is not likely to illuminate a trapped survivor squarely on the chest. It is thus important to determine if a microwave reflection from other parts of the body can be used to identify the presence of a trapped victim, as well as providing some information on the vital signs. Because this microwave technique detects the time-dependent part of the permittivity of the tissues, it can work on most any part of the body. To demonstrate this, 18 GHz reflection data were collected when the beam illuminated only: 1) the lower abdomen; 2) the left-side of the head; and 3) the upper-half of the left leg. In each case the beam impinged at near normal incidence to the tissue in the body area being measured. Other nearby body areas were covered with aluminum foil or absorber to avoid any additional modulation of the signal from those areas.

FIG. 20 is a graph showing (a) microwave signal 500 reflected from the lower abdomen; (b) the lowpass filtered microwave signal 501 and its derivative 502 The oscillating volume of blood in the illuminated tissues produces significant modulation of the reflected microwave signal, as seen in the derivative which shows a large periodic systolic peak (labeled I), followed by a smaller peak (labeled 2) which appears similar to an O-wave; and (c) the highpassed-filtered microwave cardiogram 503 and the unfiltered ECG 504. There is a reasonable correlation with structures associated with the $1^{st}$ heart sound and the QRS-complex. There is also a reproducible dip in the microwave signal 503 at the position of the T-wave (ventricular repolarization) in the ECG; as well as a smaller dip in the region of the P-wave.

Figure 21:
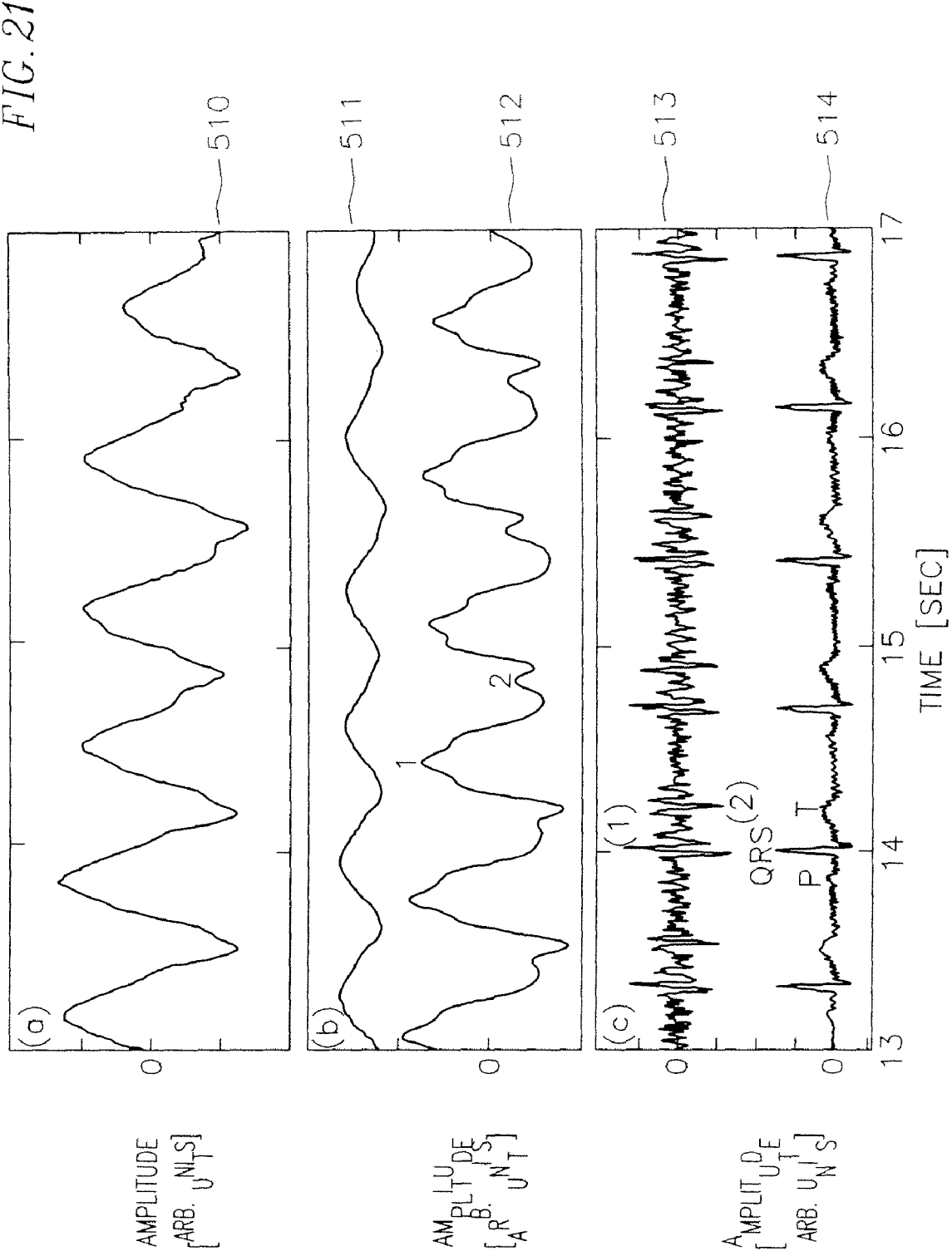
FIG. 21 is a graph showing (a) microwave signal reflected from the left side of the head; (b) the lowpass filtered microwave signal and its derivative; and (c) the highpassed-filtered microwave cardiogram and the unfiltered ECG.

FIG. 21 is a graph showing (a) microwave signal 510 reflected from the left side of the head; (b) the lowpass filtered microwave signal 511 and its derivative 512. The oscillating volume of blood in the illuminated tissues produces significant modulation of the reflected microwave signal, showing that the resulting distinctive systolic peak (labeled 1) in the derivative is clearly seen, as is a diastolic peak (labeled 2); and (c) the highpassed-filtered microwave cardiogram 513 and the unfiltered ECG 514. There is reasonable correlation between the structures related the first heart-sound, the QRS-complex, and the second heart sound. There is also a reproducible dip in the microwave signal at the position of the T-wave in the ECG.

Figure 22:
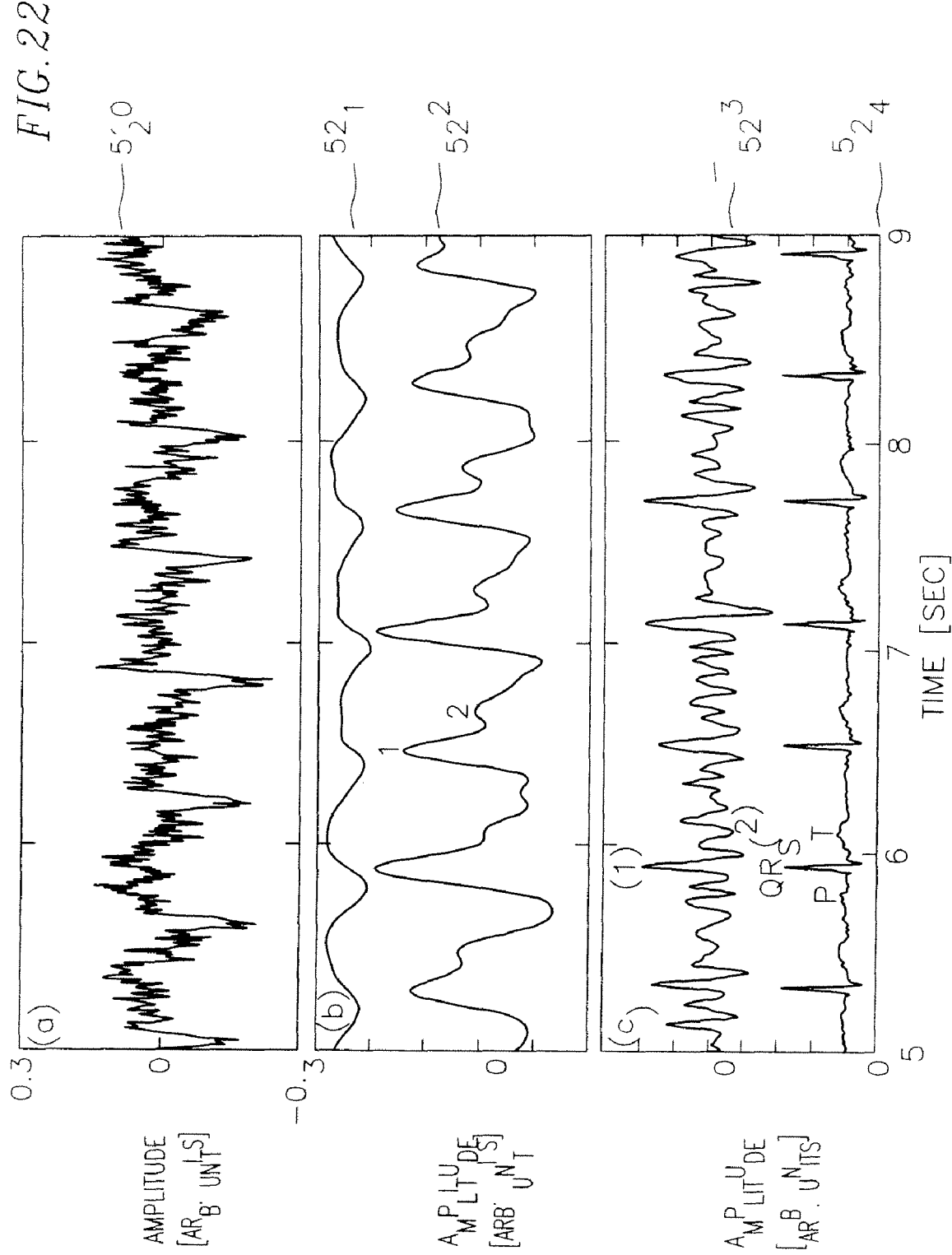
FIG. 22 is a graph showing (a) microwave signal reflected from the upper part of the left leg; (b) the lowpass filtered microwave signal and its derivative; and (c) the highpassed-filtered microwave cardiogram and the unfiltered ECG.

FIG. 22 is a graph showing (a) microwave signal 520 reflected from the upper part of the left leg; (b) the lowpass filtered microwave signal 521 and its derivative 522 (This low-frequency component is related to blood flow, and the resulting distinctive systolic peak (labeled 1) in the derivative is clearly seen, as is a diastolic peak (labeled 2).); and (c) the highpassed-filtered microwave cardiogram 523 and the unfiltered ECG 524. Again, there is reasonable correlation between the structures related to the heart sounds and the QRS-complex, though the microwave signal is noisier in this case due to the weaker modulation produced by the smaller tissue volume of the leg.

The same basic features are seen again in FIG. 22 for the measurements on the left leg. In general, the modulation of the reflected microwave signal for these other body areas was lower than for the case of illuminating the chest. In particular, the signal modulation for the case of the leg was significantly lower, resulting in the noisier waveform seen in (a). The S/N ratio will be greater the larger the fraction of the body that is illuminated. Nonetheless, this demonstrates that waveforms with unique human characteristics related to cardiac activity can be obtained from different parts of the body other than the chest. This provides an additional unique capability not generally possible with the microwave Doppler radar approach.

Given that it is possible to remotely measure cardiographic-related waveforms, there are potentially several useful, as well as commercial, applications of the remote-sensing technique described in the paper. Some have already been mentioned. To summarize, these include 1) long-term monitoring of cardiac patients; 2) search and rescue—the ability to identify survivors behind collapsed walls or other barriers, and even obtain some preliminary information on their medical condition; 3) emergency medical support—remote-sensing of some vital signs would be especially useful for burned or trapped victims; 4) NASA—unfettered monitoring of astronauts aboard the International Space Station and continuous monitoring during Extra-Vehicular Activities, as well as continuous monitoring of Shuttle pilots during takeoff and landing operations; 5) a SIDS monitor—the microwave beam would readily pass through blankets and clothing, and because the beam size can cover the entire crib, the location or position of the infant should not affect the ability to monitor pulse and respiration; 6) adult sleep apnea monitor; and 7) a portable handheld unit to monitor pulse and respiration during exercise.

The microwave components used in the measurements discussed above are readily available commercial items. The performance specifications of the components are not critical which simplifies the design and reduces cost. The entire RF part of the system could readily be mass-produced using MMIC-based techniques and automated assembly similar to cell phone manufacturing methods, thus further reducing costs and size. The antenna, battery, and readout display will determine the final size of a portable unit. For operational distances up to say 20 ft, an 18 GHz handheld unit should be only slightly larger than a PDA or handheld computer. Because the technique relies on the RF permittivity of tissues near the surface of the body, higher frequencies, up to possibly 90 GHz would also work. In this case, antenna sizes would be proportionately smaller. However, high frequencies will not penetrate certain barriers as well. The final configuration will depend on the specific application and tradeoffs will need to be made between power level, penetration capability, distance of operation, antenna size, and battery life.

It has been shown that it is possible to measure cardiographic-related waveforms, as well as the respiration rate of a person over distances of several meters using an 18 GHz remote-sensing technique. Such waveforms can also be measured through common construction banners such as walls and doors. The biomedical information is contained in the small amplitude modulations of the reflected microwave signal caused by the time-dependent part of the permittivity of the illuminated tissue, as driven by the heart. The microwave signal can be reflected from most any area of the body, though the strongest modulation is obtained from the upper torso. The RF components for a small portable device are readily available. Development of appropriate signal processing algorithms to better separate the various physiological and motion-related components of the signal could lead to devices with a variety of medical, search and rescue, and other commercial applications.

In summary, basic single-lead or multi-lead electrocardiographic (ECG) measurements are commonly used in a variety of medical situations. In short-term, non-ambulatory cases, the measurements are relatively simple to take. However, for many medical situations, the circumstances can pose real problems for the patient-electrode interface. Important examples include (1) long-term intensive care which requires continuous cardiac monitoring (electrodes usually need to be replaced at least once a day and skin irritations can result from prolonged use); (2) burn victims for which any type of physical contact is problematic; (3) victims at an accident/disaster site, or patients in an ambulance, where even the single-wire from a simple finger pulse-oximeter may interfere with the work of emergency medical technicians; and (4) measurements of heart conditions that occur sporadically, requiring the patient to wear a Halter monitor for 24-48 hours. In cases like these, a method for obtaining electrocardiographic-related data without contacting the patient, and even from a distance of several meters away, would significantly benefit the patient and improve the medical care. An additionally important application of such a capability would be to allow rescue workers to locate survivors behind collapsed walls or floors, or under rubble piles, by remotely-sensing a human cardiographic waveform and respiration. This would help to save lives, since for example it takes two hours for trained rescue personnel to cut a 1 m² hole through a 6-inch thick reinforced concrete wall. Determining first whether anyone is alive behind various barriers and deploying resources appropriately is critical to rescuing as many people as possible. Improvements in technologies, to locate survivors is a high priority for disaster assistance and rescue teams.

Figure 23:
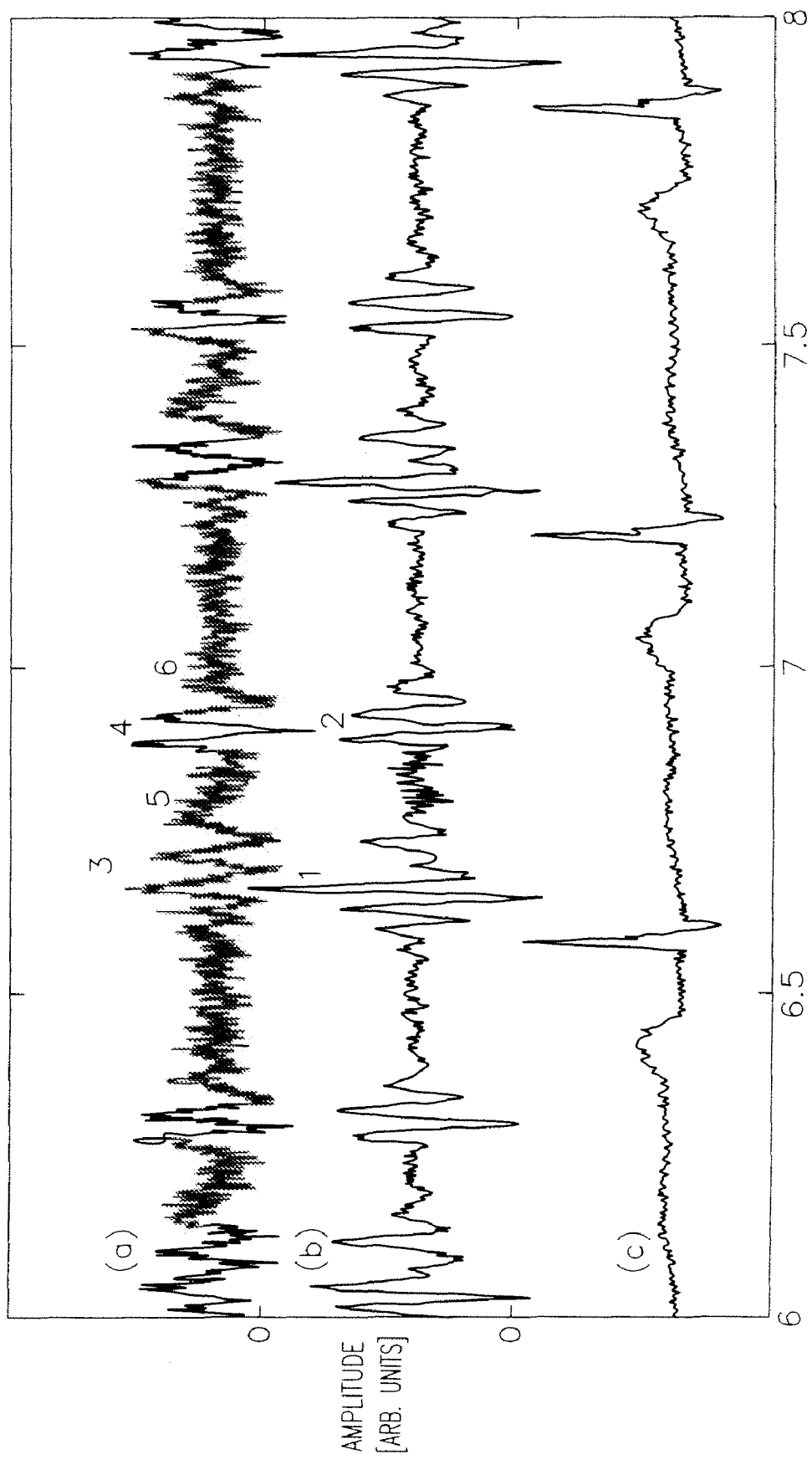
FIG. 23 is a graph showing (a) a highpass-filtered microwave cardiogram obtained from illuminating the torso; (b) the simultaneously measured phonocardiogram; (c) The ECG measured for reference. The first and second heart sounds are labeled in curve (b) as 1 and 2, respectively. The relevant points on the microwave cardiogram, curve (a), corresponding to correlated features in the PCG (curve (b)), and ECG (curve (c)), are labeled 3 through 6.
Figure 13:
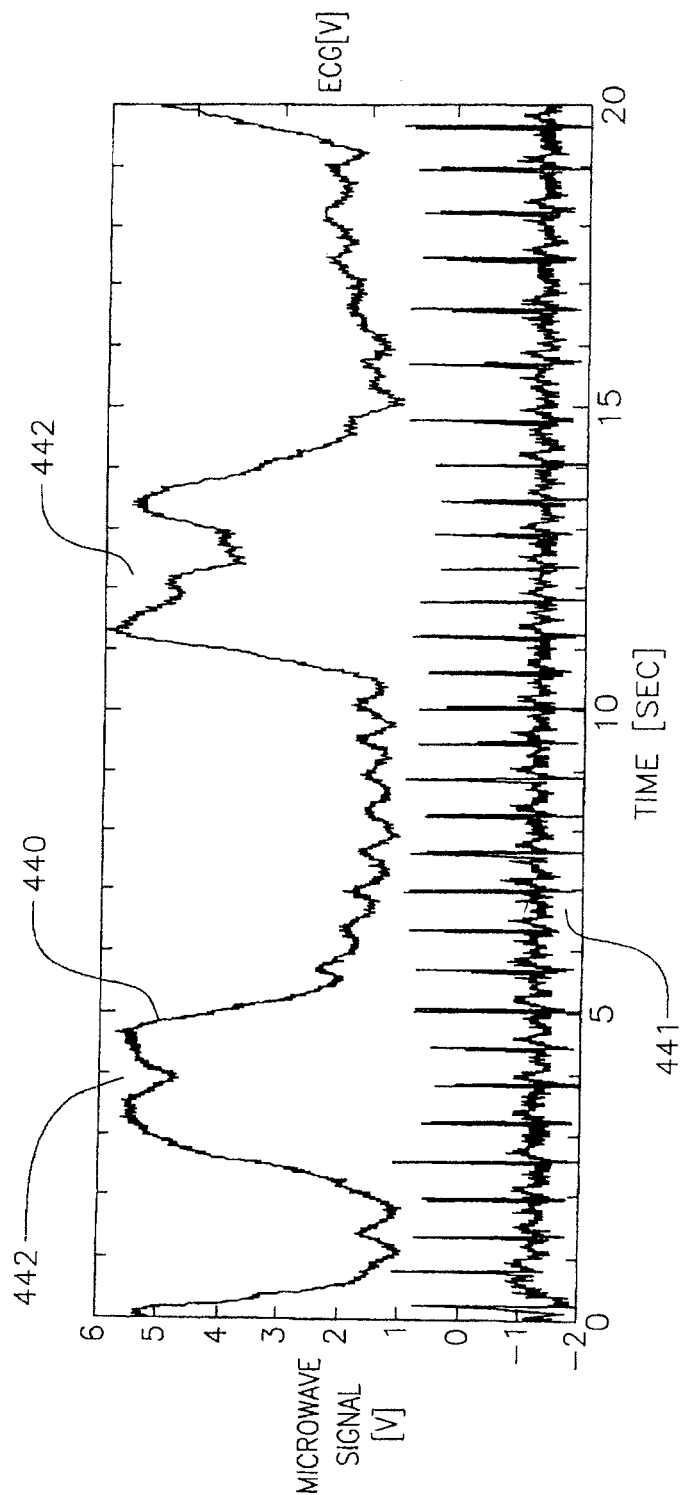

As previously mentioned, a small amount of the transmitter source signal leaks into the receiver signal path. As a result, any small phase shifts in the reflected signal from the subject due to motion, will interfere constructively and destructively with the fixed leakage signal. This will produce amplitude changes in the detected signal. Due to the very high frequency, and hence very short wavelength, of our test system, this interference-effect produces measurable amplitude changes due to very tiny motions in the illuminated tissue. As a result, our test system can readily detect the small vibrations due to the heart sounds. FIG. 23 shows three measured curves for an adult male sitting about 3 feet from the transmitting antenna. Curve (c) shows the contacting ECG, for reference. Curve (b) shows the waveforms of the first (label 1) and second (label 2) heart sounds obtained with the accelerometer. This waveform is commonly referred to as a phonocardiogram (PCG). This curve was highpass filtered with a corner frequency of 20 Hz. (This just removed any baseline drifts, as the heart sounds have dominate frequency components above 20 Hz, anyway.) Curve (a) shows the microwave cardiogram after highpass filtering above 20 Hz. As can be seen there is exceptionally close correlation with the PCG.

The peaks, labeled 3 and 4, align extremely well with the first, 1, and second, 2, heart sounds, respectively. Even the structure and shapes of the corresponding peaks is very similar. This clearly indicates that this approach can be used to detect details in the heart sounds, which would be useful for diagnostic purposes. Heart murmurs, and other anomalous sounds could be readily monitored from a large distance. It is also interesting to note, that structures corresponding to parts of the ECG are also present in the microwave waveform. For example, the reproducible slope, labeled 5, between the $1^{st}$ and $2^{nd}$ sounds, aligns very well with the downward sloping side of the T-wave. There is also a reproducible dip, labeled 6, well aligned with the P-wave.

While the above description contains many specific embodiments of the invention, these should not be construed as limitations on the scope of the invention, but rather as an example of one embodiment thereof. Many other variations are possible, including implementing remote-detection systems in accordance with the present invention using planar antennas and MMIC manufacturing techniques. In addition, any process, physiological or otherwise, can be monitored that involves variations in patterns and/or intensity of reflected electromagnetic radiation using remote-detection systems in accordance with the present invention. Accordingly, the scope of the invention should be determined not by the embodiments illustrated, but by the appended claims and their equivalents.

While the invention has been described in terms of exemplary embodiments, it is to be understood that the words which have been used are words of description and not of limitation. As is understood by persons of ordinary skill in the art, a variety of modifications can be made without departing from the scope of the invention defined by the following claims, which should be given their fullest, fair scope.

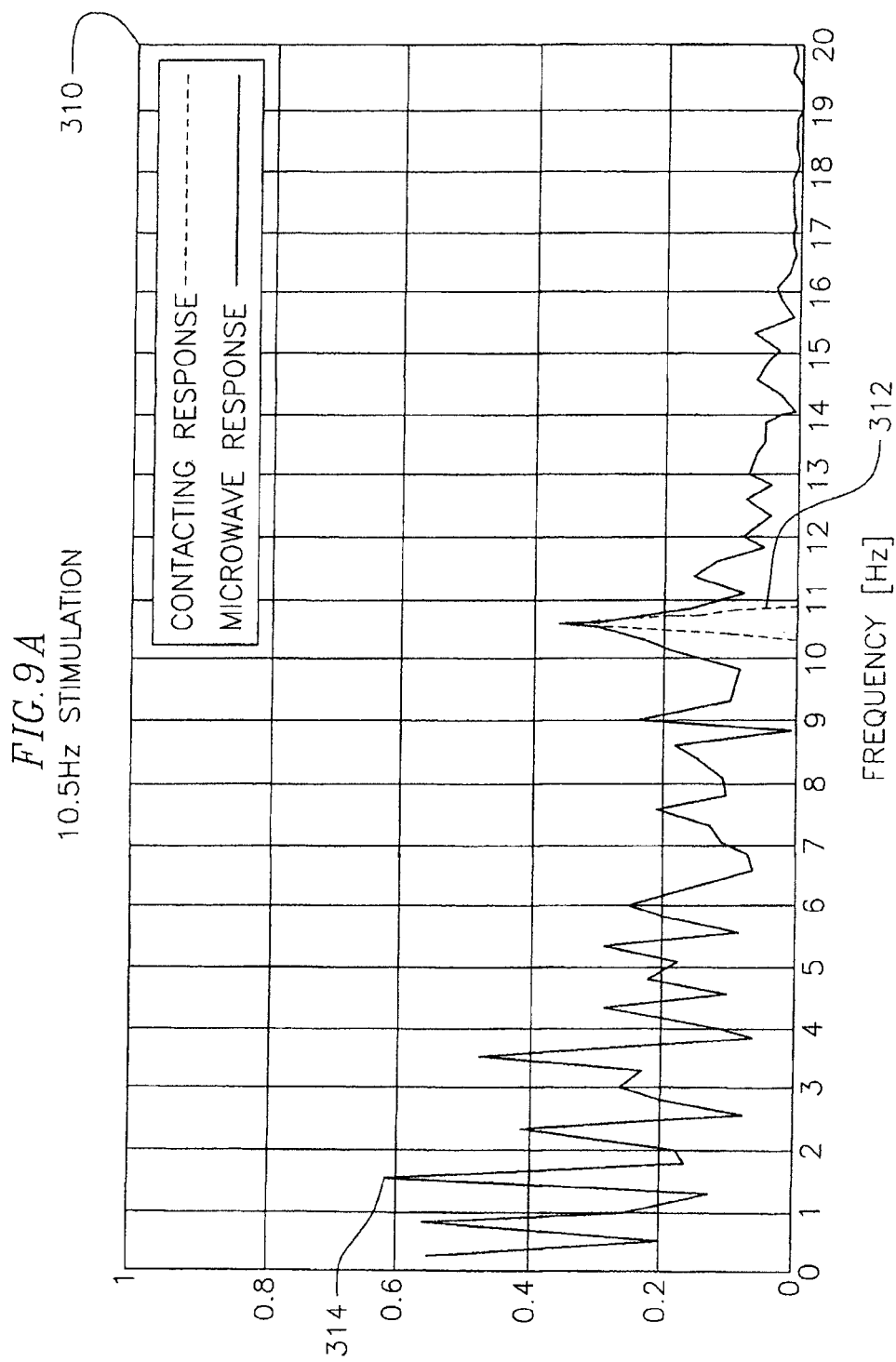

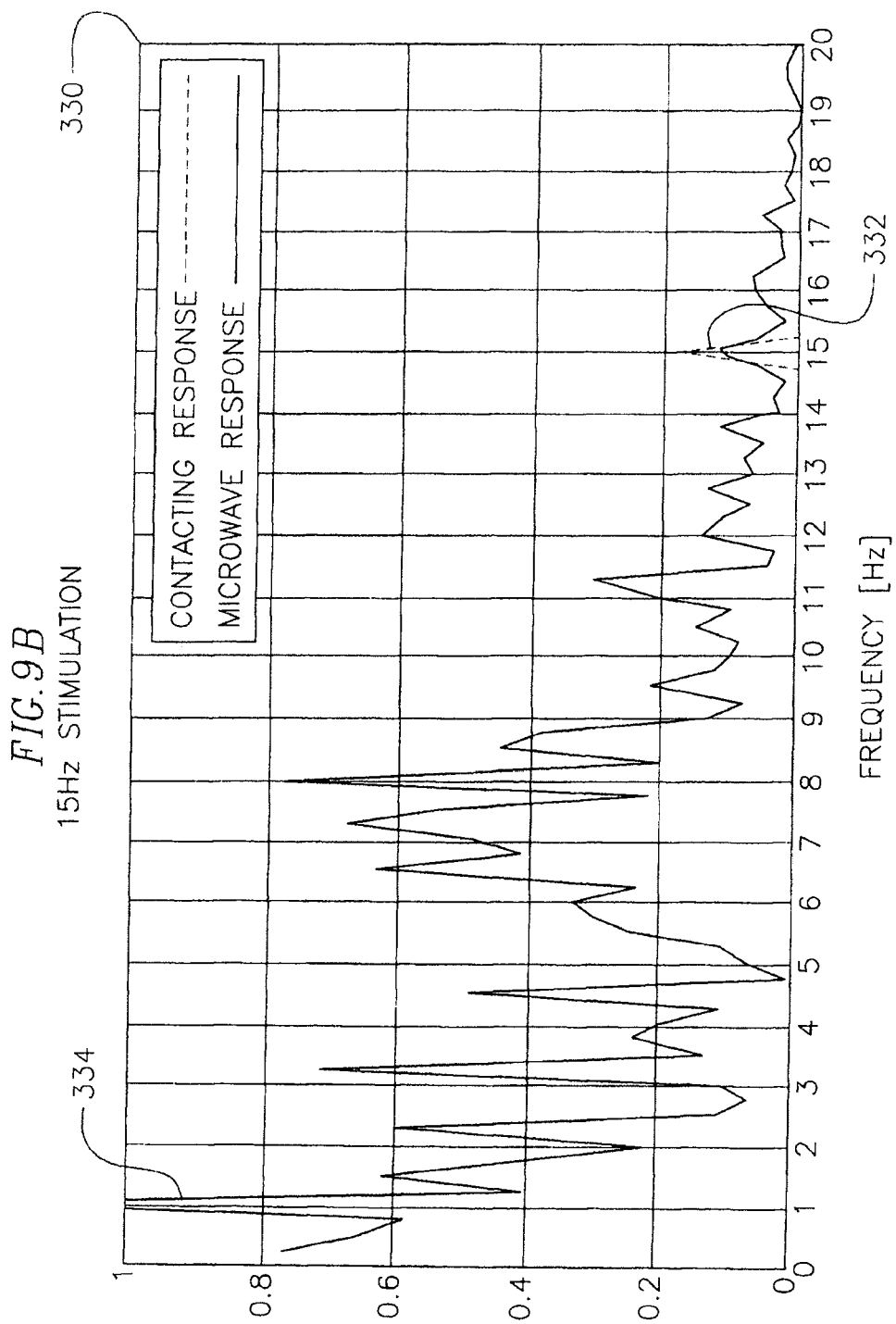

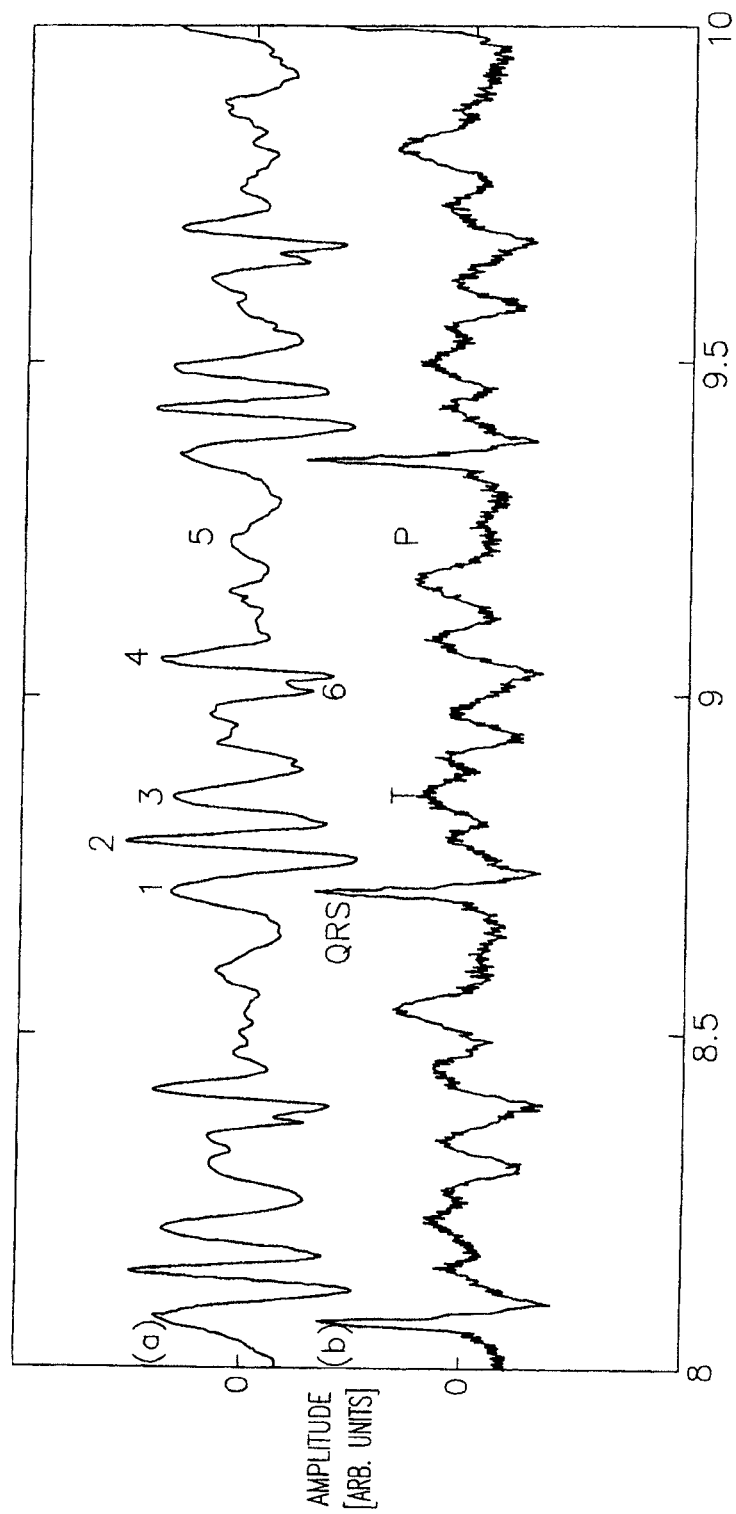

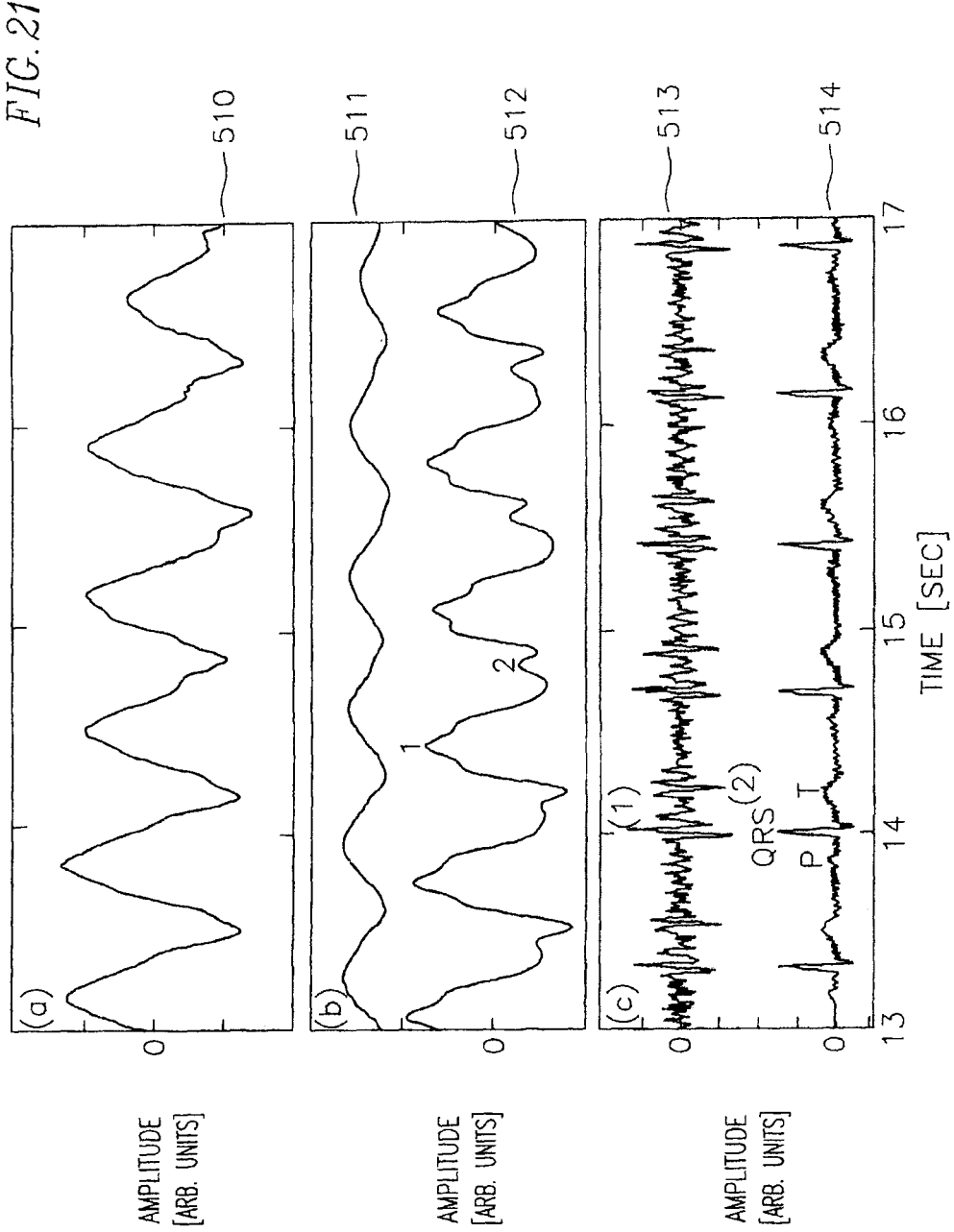

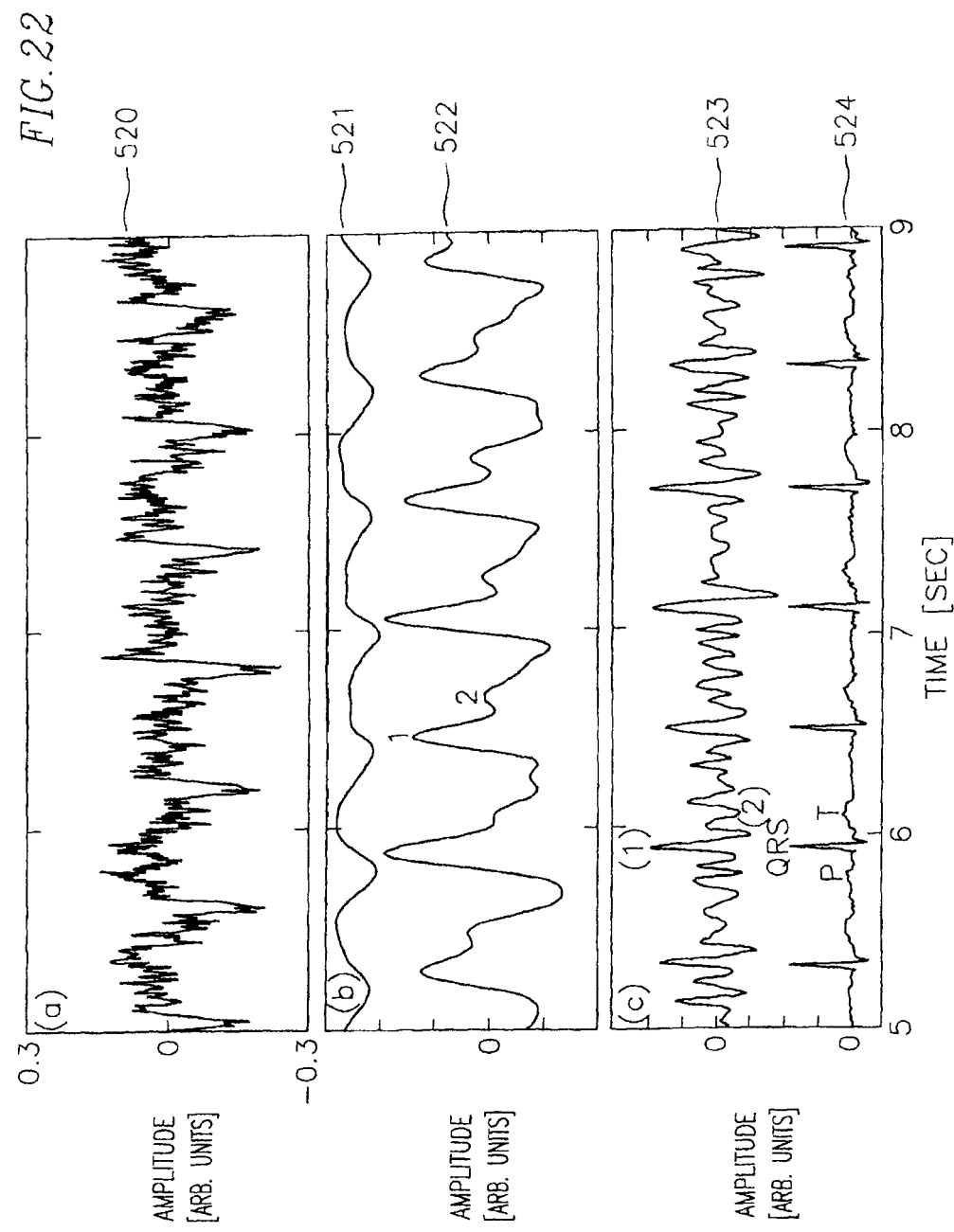

What is claimed is:

1. A non-imaging remote-detection system for monitoring changes in permittivity associated with cardiac-related activity of a subject having a body that is free to move, comprising:
 a source containing an oscillator configured to illuminate tissue of the subject with an electromagnetic signal beam;
 a receiver configured to receive reflections of the electromagnetic signal beam from the subject, where the reflections include amplitude variations indicative of motion of the illuminated tissue and amplitude variations indicative of time dependent variations in a reflection coefficient at an air-tissue interface of the subject's body resulting from variations in the permittivity of the illuminated tissue associated with electrical activity of the subject's heart; and
 a detector connected to the receiver and configured to extract from the reflected signal beam the variations in amplitude indicative of time dependent variations in the reflection coefficient.

2. The remote-detection system of claim 1, wherein:
 the source also includes a first antenna portion; and
 the receiver includes a second antenna portion connected to the detector.

3. The remote-detection system in claim 2, wherein the source and the receiver are directionally coupled to a single antenna that acts as the first antenna portion and the second antenna portion.

4. The remote-detection system of claim 1, wherein:
 the subject has a beating heart;
 the permittivity of the illuminated tissue changes in response to the beating heart;

the amplitude of the reflected electromagnetic signal beam changes as the permittivity of the illuminated tissue changes; and the detector is configured to extract from the reflected electromagnetic signal beam variations in amplitude associated with the changes in the permittivity of the illuminated tissue.

5. The remote-detection system of claim 1, wherein the detector is further configured to extract from the reflected signal beam the variations in amplitude indicative of motion of the illuminated tissue.

6. The remote-detection system of claim 5, wherein:

the detector is configured to extract from the reflected signal beam the variations in amplitude indicative of motion of the illuminated tissue as correlates with heart sounds or a phonocardiogram of the subject.

7. A non-imaging remote-detection system for monitoring the cardiac-related activity of a subject having a body, comprising:

means for illuminating tissue of the subject with an electromagnetic signal;

means for detecting reflections of the electromagnetic signal, where the reflections include amplitude variations indicative of motion of the illuminated tissue and amplitude variations indicative of time dependent variations in a reflection coefficient at an air-tissue interface of the subject's body resulting from variations in the permittivity of the illuminated tissue associated with electrical activity of the subject's heart; and means for extracting a signal indicative of the amplitude variations of the electromagnetic signal reflected by the illuminated tissue that are associated with motion of the illuminated tissue and the amplitude variations of the electromagnetic signal reflected by the illuminated tissue that are associated with time dependent changes in the reflection coefficient.

8. The remote-detection system as claimed in claim 7, further comprising:

means for extracting a signal indicative of the changes in the amplitude of the electromagnetic signal reflected by the illuminated tissue that are associated with motion of the illuminated tissue as correlates with heart sounds or a phonocardiogram of the subject.

9. A non-imaging method of observing changes in the permittivity of a body of a subject associated with cardiac-related activity, comprising:

illuminating tissue of the subject with an electromagnetic signal beam;

receiving reflections of the electromagnetic signal beam that include amplitude variations indicative of motion of the illuminated tissue and amplitude variations indicative of time dependent variations in a reflection coefficient at an air-tissue interface of the subject's body resulting from variations in the permittivity of the illuminated tissue associated with electrical activity of the subject's heart; and extracting from the reflected signal a signal indicative of the amplitude variations of the electromagnetic signal associated with motion of the illuminated tissue and the amplitude variations of the electromagnetic signal associated with time dependent changes in the reflection coefficient.

10. The method of claim 9, further comprising:

extracting from the reflected signal a signal indicative of the changes in the amplitude of the electromagnetic signal associated with motion of the illuminated tissue as correlates with heart sounds or a phonocardiogram of the subject.

11. A non-imaging remote sensing system for providing cardiac-related data of a subject having a body, comprising:

a transmitter for transmitting a microwave signal to illuminate tissue of the subject;

a receiver for receiving a reflected microwave signal, the reflected microwave signal being a reflection of the microwave signal from illuminated tissue of the subject; and a processor for processing the reflected microwave signal;

wherein the processor is configured to analyze an amplitude of the reflected microwave signal to determine changes in a reflection coefficient at an air-tissue interface of the subject's body resulting from changes in permittivity of the illuminated tissue of the subject, the changes in permittivity containing a static component and a time-varying component, the processor being configured to process the time-varying component to provide cardiographic related data of the subject.

12. The remote sensing system as claimed in claim 11, wherein:

the transmitter includes an RF oscillator coupled to a circulator and an antenna coupled to the circulator;

the receiver includes the antenna coupled to the circulator; and the processor includes an amplifier, a direct detector, and a computer.

13. The remote sensing system as claimed in claim 11, wherein the microwave signal has a frequency between 100 MHz and 200 GHz.

14. A remote sensing system for providing cardiac-related data of a subject, comprising:

a transmitter for transmitting a microwave signal to illuminate tissue of the subject;

a receiver for receiving a reflected microwave signal, the reflected microwave signal being a reflection of the microwave signal from illuminated tissue of the subject; and a processor for processing the reflected microwave signal;

wherein the processor is configured to analyze an amplitude of the reflected microwave signal to determine changes in permittivity of the illuminated tissue of the subject, the changes in permittivity containing a static component and a time-varying component, the processor being configured to process the time-varying component to provide cardiographic related data of the subject;

wherein the cardiographic related data correlate with an electrocardiogram or an impedance cardiogram.

15. A remote sensing system for providing cardiac-related data of a subject, comprising:

a transmitter for transmitting a microwave signal to illuminate tissue of the subject;

a receiver for receiving a reflected microwave signal, the reflected microwave signal being a reflection of the microwave signal from illuminated tissue of the subject; and a processor for processing the reflected microwave signal;

wherein the processor is configured to analyze an amplitude of the reflected microwave signal to determine changes in permittivity of the illuminated tissue of the subject, the changes in permittivity containing a static component and a time-varying component, the processor being configured to process the time-varying component to provide cardiographic related data of the subject;

wherein the processor is further configured to process the time-varying component to provide a respiratory pattern or a pulse rate of the subject.

16. A non-imaging method of remotely sensing cardiac-related data of a subject, comprising:

transmitting a microwave signal to illuminate tissue of the subject;

receiving a reflected microwave signal, the reflected microwave signal being a reflection of the microwave signal from illuminated tissue of the subject;

processing the reflected microwave signal and analyzing an amplitude of the reflected microwave signal to determine changes in a reflection coefficient at an air-tissue interface of the subject's body resulting from changes in permittivity of the illuminated tissue of the subject, the changes in permittivity containing a static component and a time-varying component; and processing the time-varying component to provide cardiographic related data of the subject.

17. The method as claimed in claim 16, further comprising:
A method of remotely sensing cardiac-related data of a subject, comprising:

transmitting a microwave signal to illuminate tissue of the subject;

receiving a reflected microwave signal, the reflected microwave signal being a reflection of the microwave signal from illuminated tissue of the subject;

processing the reflected microwave signal and analyzing an amplitude of the reflected microwave signal to determine changes in permittivity of the illuminated tissue of the subject, the changes in permittivity containing a static component and a time-varying component; and processing the time-varying component to provide cardiographic related data of the subject;

providing a respiratory pattern or a pulse rate from the time-varying component.

18. The method as claimed in claim 16, wherein the microwave signal has a frequency between 100 MHz and 200 GHz.

19. A method of remotely sensing cardiac-related data of a subject, comprising:

transmitting a microwave signal to illuminate tissue of the subject;

receiving a reflected microwave signal, the reflected microwave signal being a reflection of the microwave signal from illuminated tissue of the subject;

processing the reflected microwave signal and analyzing an amplitude of the reflected microwave signal to determine changes in permittivity of the illuminated tissue of the subject, the changes in permittivity containing a static component and a time-varying component; and processing the time-varying component to provide cardiographic related data of the subject;

providing the cardiographic related data as correlated with an electrocardiogram or an impedance cardiogram.

* * * * *

UNITED STATES PATENT AND TRADEMARK OFFICE
CERTIFICATE OF CORRECTION

| | | |
|---|---|---|
| PATENT NO. | : 7,811,234 B2 | Page 1 of 10 |
| APPLICATION NO. | : 11/897884 | |
| DATED | : October 12, 2010 | |
| INVENTOR(S) | : William R. McGrath | |

It is certified that error appears in the above-identified patent and that said Letters Patent is hereby corrected as shown below:

In the Claims

FIG. 9A, Sheet 9 of 24    Delete Drawing Sheet 9 and substitute therefore the Drawing Sheet, consisting of FIG 9A, as shown on the attached page FIG. 9B, Sheet 10 of 24    Delete Drawing Sheet 10 and substitute therefore the Drawing Sheet, consisting of FIG 9B, as shown on the attached page FIG. 13, Sheet 14 of 24    Delete Drawing Sheet 14 and substitute therefore the Drawing Sheet, consisting of FIG 13, as shown on the attached page FIG. 14, Sheet 15 of 24    Delete Drawing Sheet 15 and substitute therefore the Drawing Sheet, consisting of FIG 14, as shown on the attached page FIG. 17, Sheet 18 of 24    Delete Drawing Sheet 18 and substitute therefore the Drawing Sheet, consisting of FIG 17, as shown on the attached page FIG. 18, Sheet 19 of 24    Delete Drawing Sheet 19 and substitute therefore the Drawing Sheet, consisting of FIG 18, as shown on the attached page FIG. 21, Sheet 22 of 24    Delete Drawing Sheet 22 and substitute therefore the Drawing Sheet, consisting of FIG 21, as shown on the attached page Signed and Sealed this
Fourth Day of October, 2011

David J. Kappos
*Director of the United States Patent and Trademark Office*

FIG. 22, Sheet 23 of 24    Delete Drawing Sheet 23 and substitute therefore the Drawing Sheet, consisting of FIG 22, as shown on the attached page